(12) United States Patent
Thottathil

(10) Patent No.: US 9,987,269 B2
(45) Date of Patent: Jun. 5, 2018

(54) ALPHA-HYDROXY CARBOXYLIC ACID AND DERIVATIVES AND OTHER GRAS-BASED PRODRUGS OF OXYMORPHONE AND USES THEREOF

(71) Applicant: 3ST Research LLC, Westfield, NJ (US)

(72) Inventor: John K. Thottathil, Mundelein, IL (US)

(73) Assignee: 3ST Research LLC, Westfield, NJ (US)

( * ) Notice: Subject to any disclaimer, the term of this patent is extended or adjusted under 35 U.S.C. 154(b) by 0 days. days.

(21) Appl. No.: 14/956,143

(22) Filed: Dec. 1, 2015

(65) Prior Publication Data

US 2017/0151228 A1 Jun. 1, 2017
US 2017/0273973 A9 Sep. 28, 2017

Related U.S. Application Data

(60) Provisional application No. 62/153,157, filed on Apr. 27, 2015.

(51) Int. Cl.
  *A01N 43/42* (2006.01)
  *A61K 31/44* (2006.01)
  *A61K 31/485* (2006.01)
  *A61K 47/54* (2017.01)
  *A61K 9/00* (2006.01)

(52) U.S. Cl.
  CPC .......... *A61K 31/485* (2013.01); *A61K 9/0053* (2013.01); *A61K 47/543* (2017.08)

(58) Field of Classification Search
  USPC ....................................................... 514/282
  See application file for complete search history.

(56) References Cited

U.S. PATENT DOCUMENTS

| | | |
|---|---|---|
| 4,673,679 A | 6/1987 | Aungst et al. |
| 7,375,083 B2 | 5/2008 | Mickle et al. |
| 8,816,083 B2 | 8/2014 | Mickle et al. |
| 2005/0075361 A1 | 4/2005 | Wang |
| 2005/0080012 A1 | 4/2005 | Mickle et al. |
| 2010/0286186 A1* | 11/2010 | Franklin ............ A61K 31/485 514/282 |
| 2011/0040072 A1 | 2/2011 | Mickle et al. |
| 2014/0200235 A1 | 7/2014 | Riggs-Sauthier et al. |
| 2016/0326182 A1 | 11/2016 | Peltier et al. |

OTHER PUBLICATIONS

Aquina, C.T., et al., OxyContin Abuse and Overdose, *Postgrad Med.* vol. 121, Issue 2 Mar. 2009, 163-67.
Non-Final Office Action in U.S. Appl. No. 14/953,392 dated Jan. 13, 2017, 15 pages.
PCT International Search Report and Written Opinion in PCT/US16/63834 dated Jan. 31, 2017, 17 pages.
PCT International Search Report and Written Opinion in PCT/US16/63836 dated Jan. 24, 2017, 17 pages.

* cited by examiner

*Primary Examiner* — Marcos L Sznaidman
(74) *Attorney, Agent, or Firm* — Servilla Whitney LLC

(57) ABSTRACT

The invention describes pharmaceutical compounds and compositions comprised of a ligand attached to the opioid oxymorphone, in a manner that substantially decreases or deters the potential for opioid abuse, addiction, illicit and illegal use, and overdose. When delivered at the proper dosage, the pharmaceutical composition provides therapeutic activity similar to that of the parent active agent.

6 Claims, 21 Drawing Sheets

Fig 1: Rat oral PK profile of oxymorphone prodrug conjugate, Formula 2
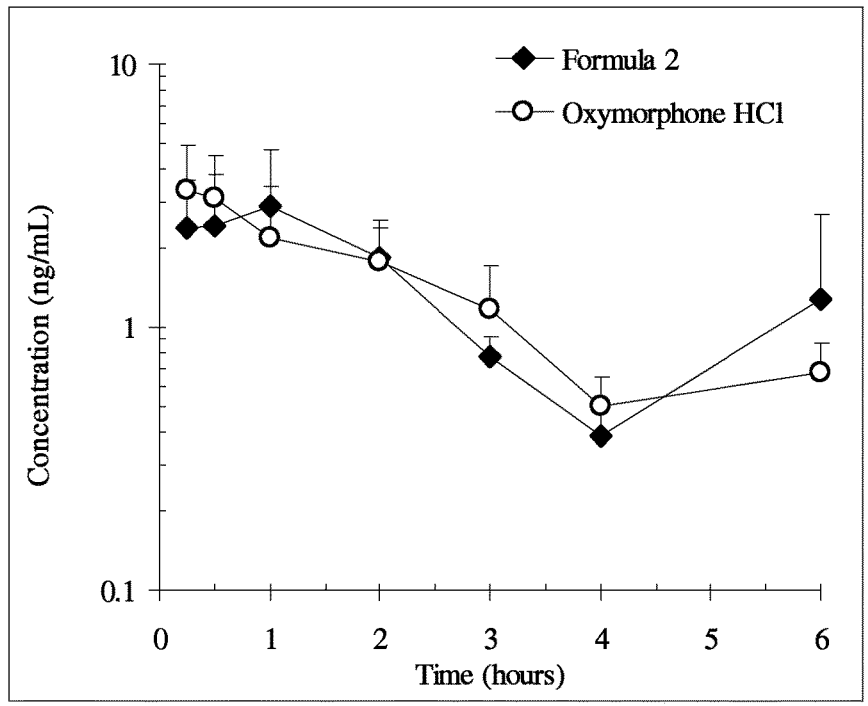
Fig 2: Rat oral PK profile of oxymorphone prodrug conjugate, Formula 3
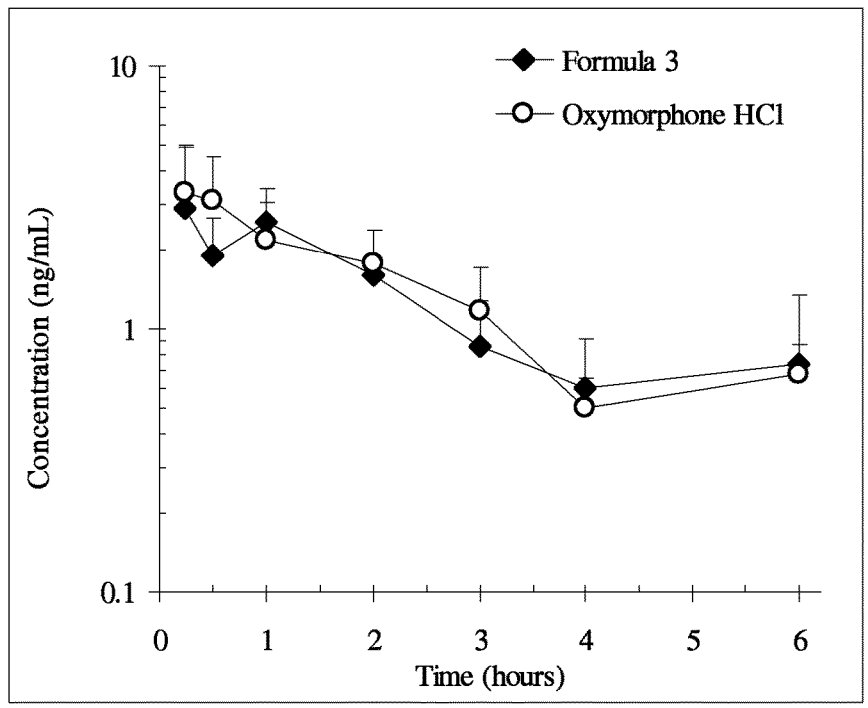

Fig 3: Rat oral PK profile of oxymorphone prodrug conjugate, Formula 4
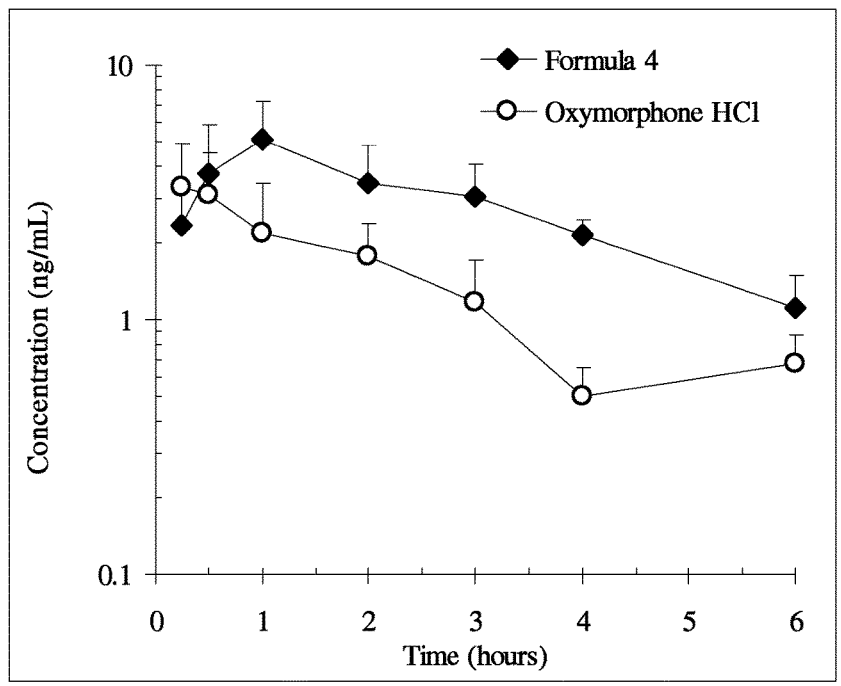
Fig 4: Rat oral PK profile of oxymorphone prodrug conjugate, Formula 5
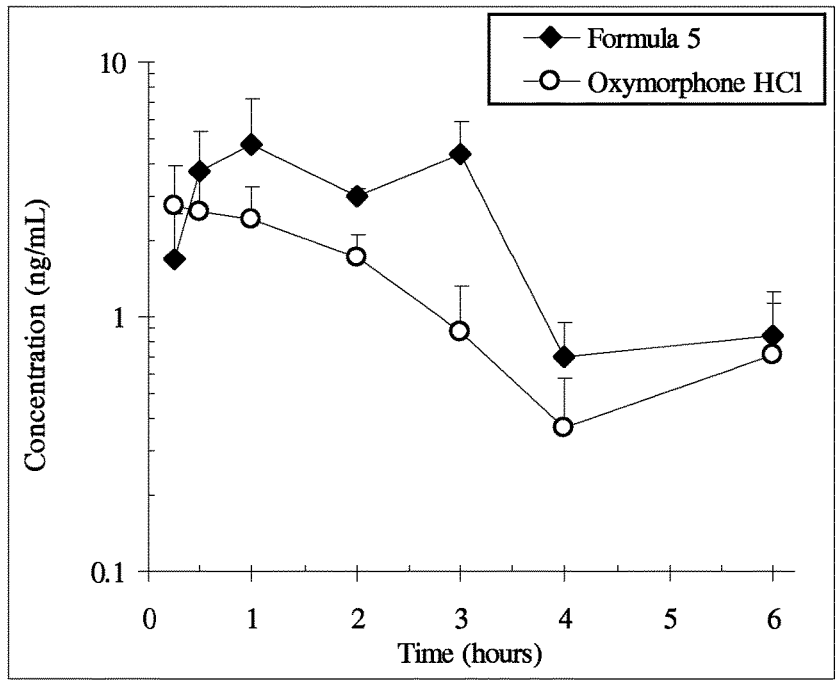

Fig 5: Rat oral PK profile of oxymorphone prodrug conjugate, Formula 6
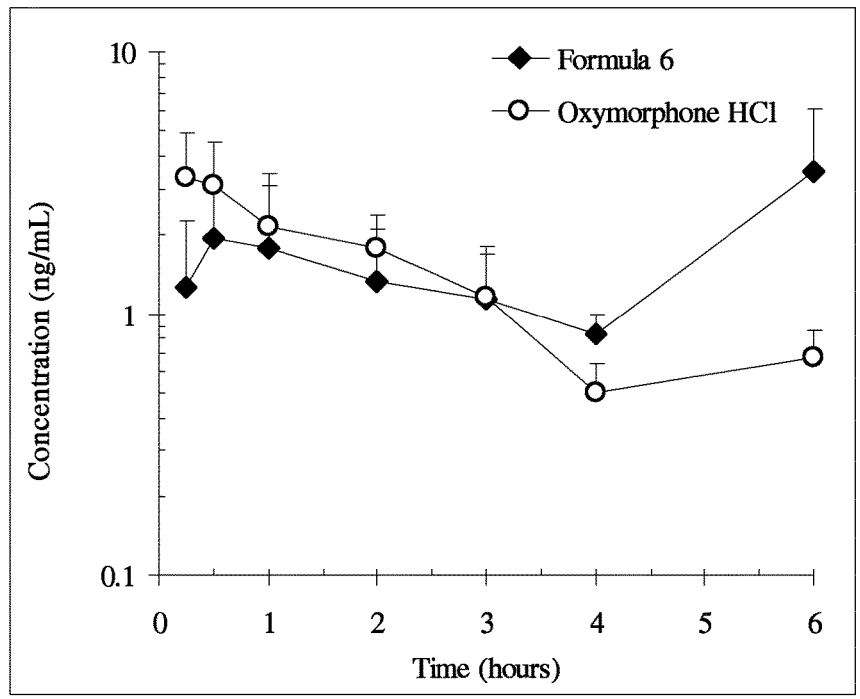
Fig 6: Rat oral PK profile of oxymorphone prodrug conjugate, Formula 7
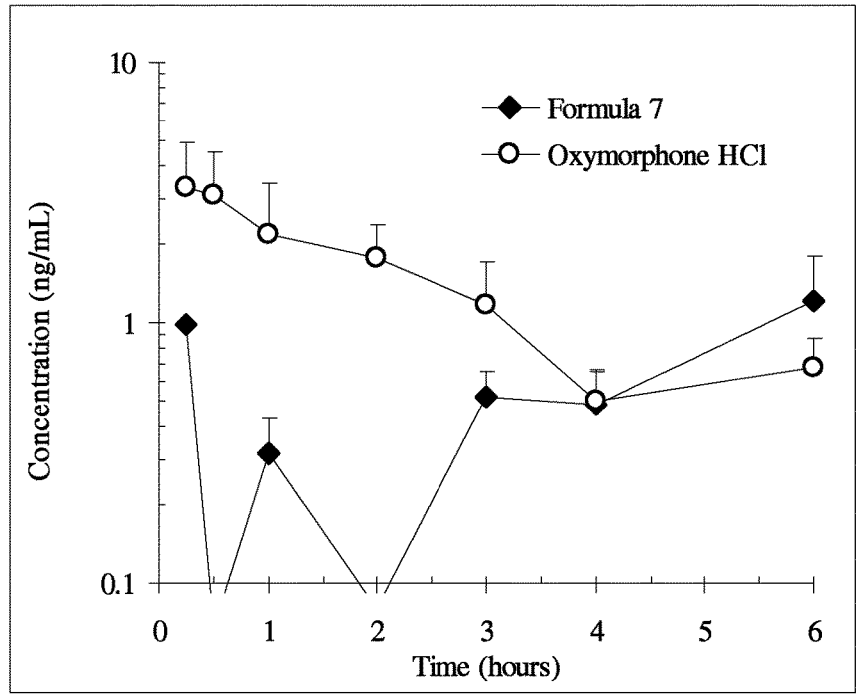

Fig 7: Rat oral PK profile of oxymorphone prodrug conjugate, Formula 8
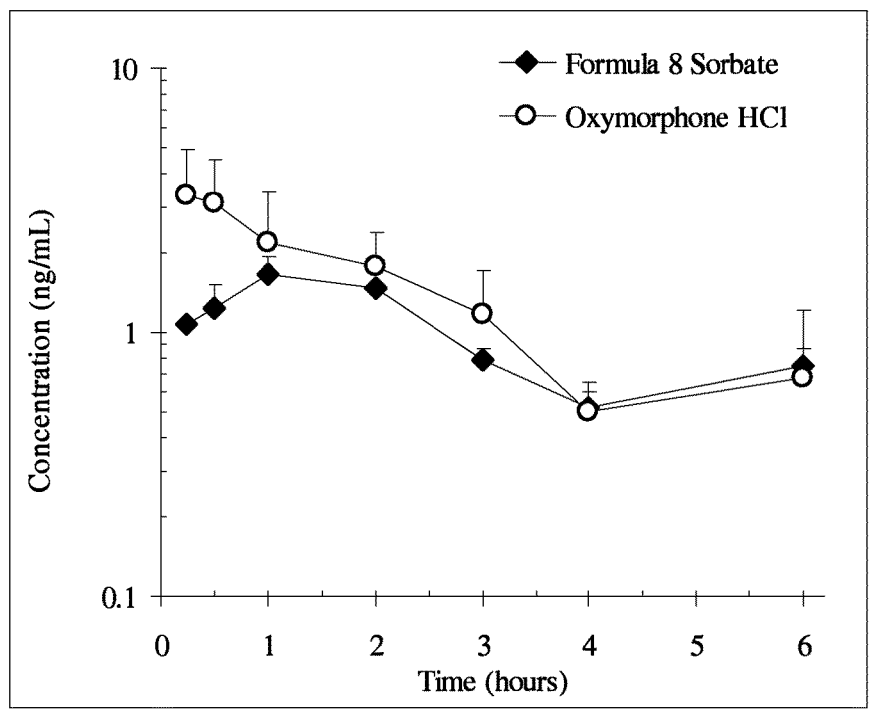
Fig 8: Rat oral PK profile of oxymorphone prodrug conjugate, Formula 9
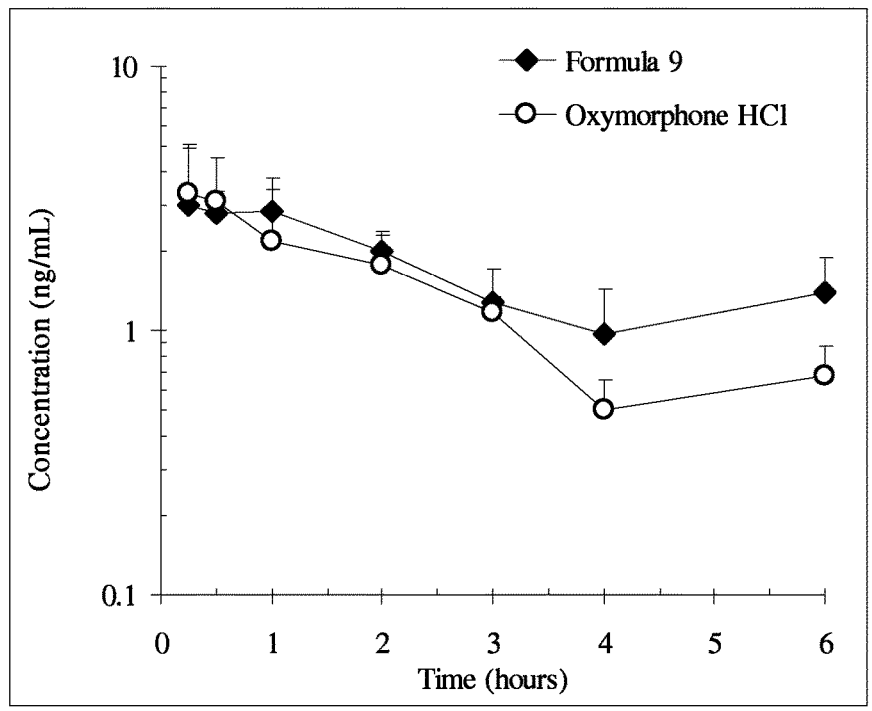

Fig 9: Rat oral PK profile of oxymorphone prodrug conjugate, Formula 10
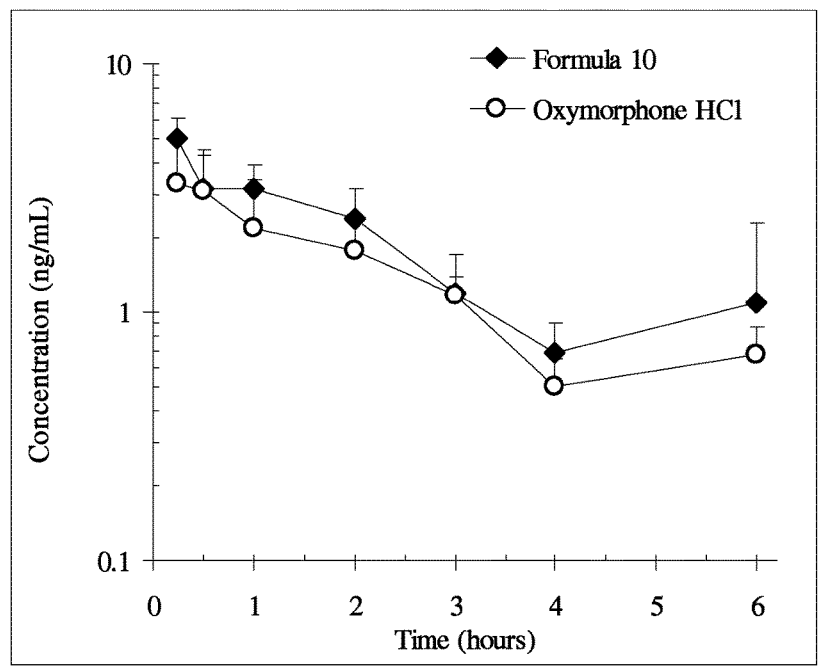
Fig 10: Rat oral PK profile of oxymorphone prodrug conjugate, Formula 11
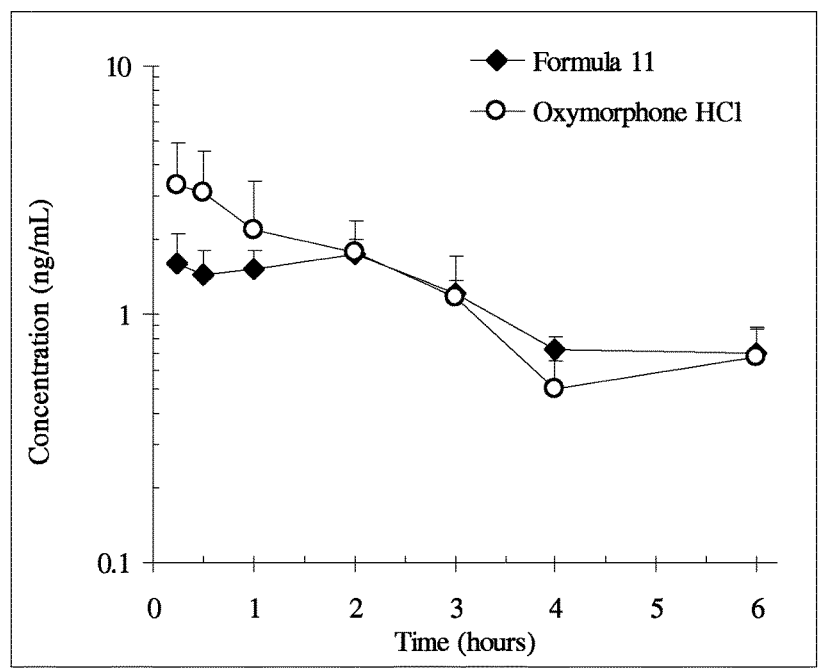

Fig 11: Rat oral PK profile of oxymorphone prodrug conjugate, Formula 12
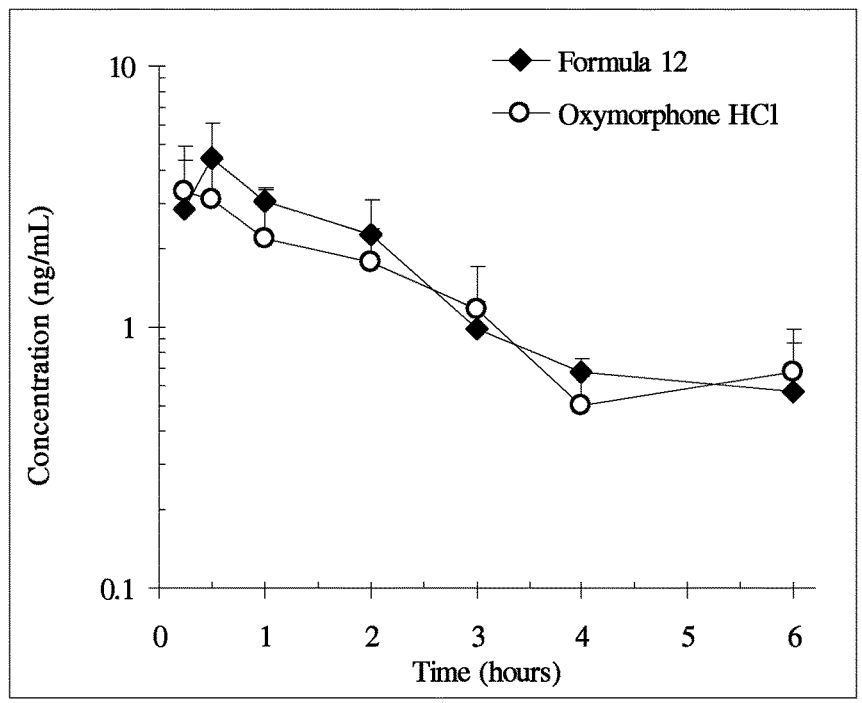
Fig 12: Rat oral PK profile of oxymorphone prodrug conjugate, Formula 14
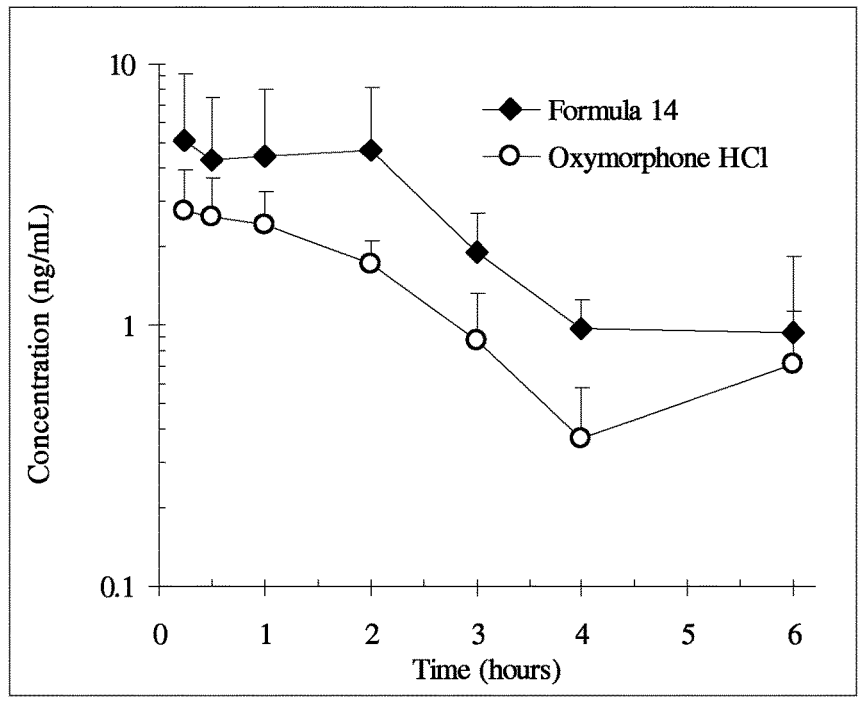

Fig 13: Rat oral PK profile of oxymorphone prodrug conjugate, Formula 16
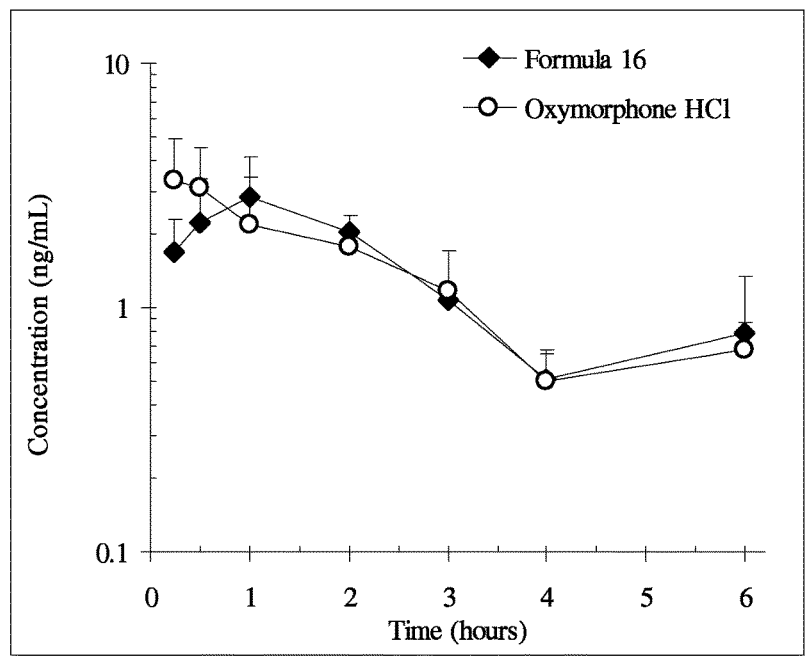
Fig 14: Rat oral PK profile of oxymorphone prodrug conjugate, Formula 18
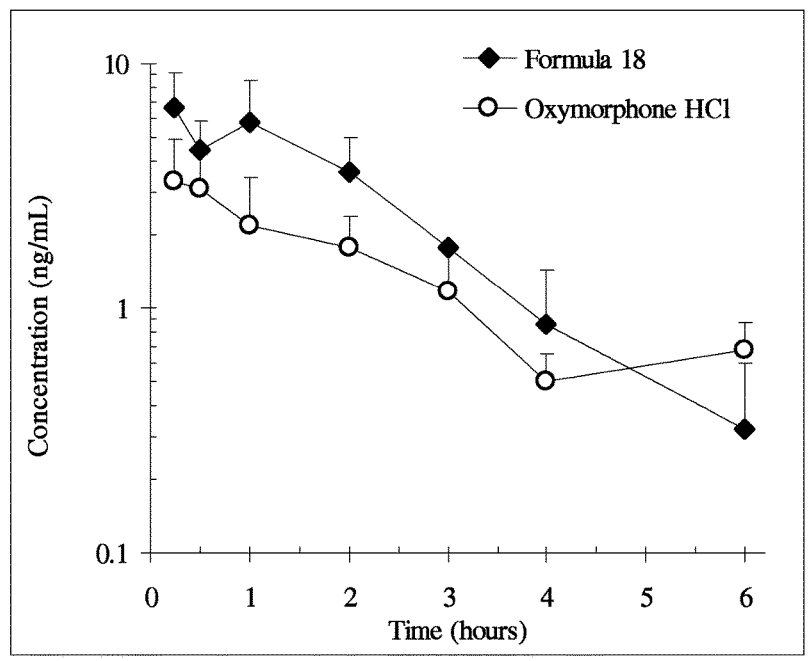

Fig 15: Rat oral PK profile of oxymorphone prodrug conjugate, Formula 19
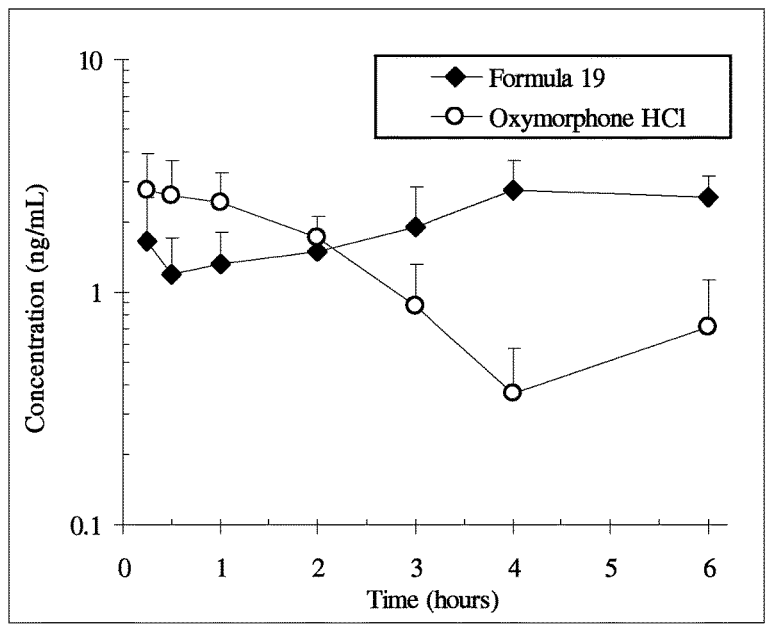
Fig 16: Rat oral PK profile of oxymorphone prodrug conjugate, Formula 21
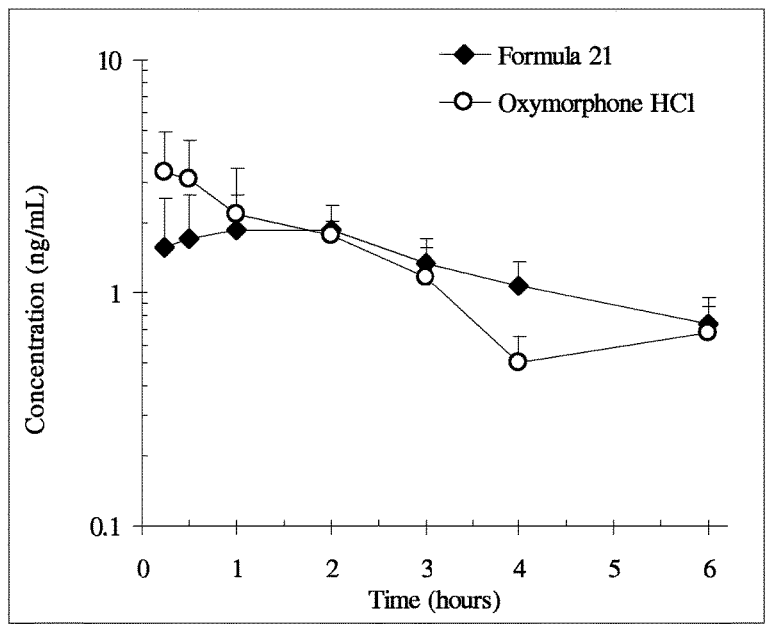

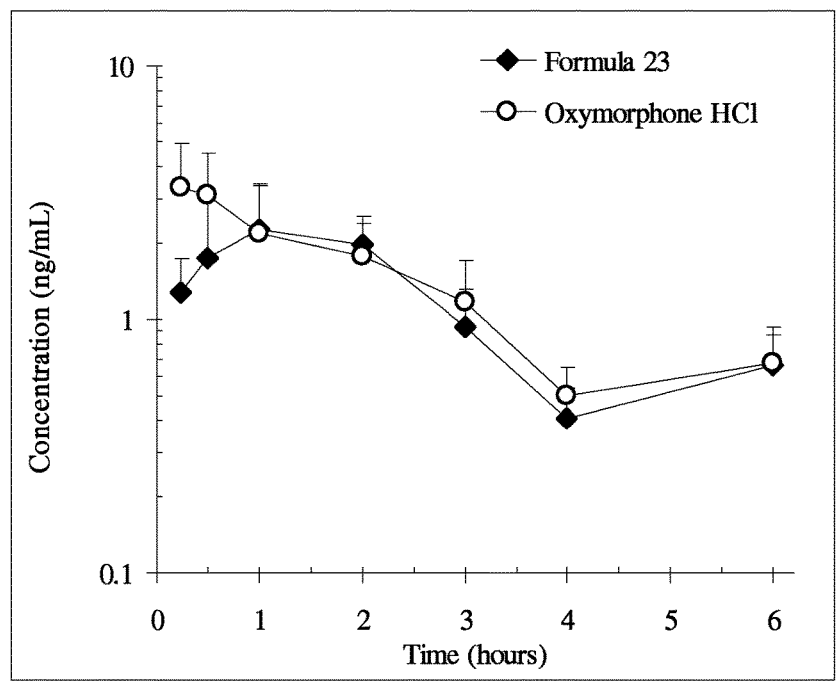
Fig 17: Rat oral PK profile of oxymorphone prodrug conjugate, Formula 23
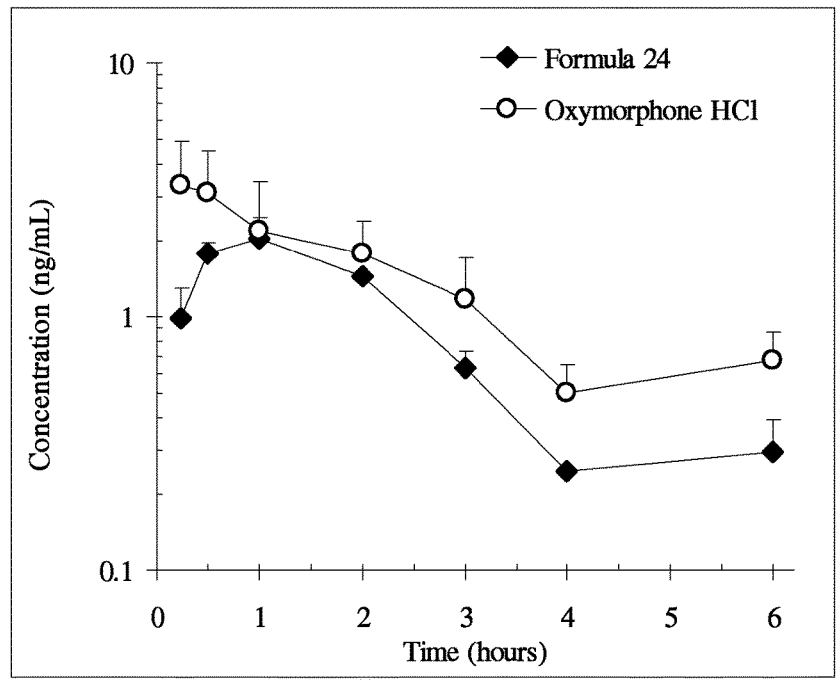
Fig 18: Rat oral PK profile of oxymorphone prodrug conjugate, Formula 24

Fig 19: Rat oral PK profile of oxymorphone prodrug conjugate, Formula 25
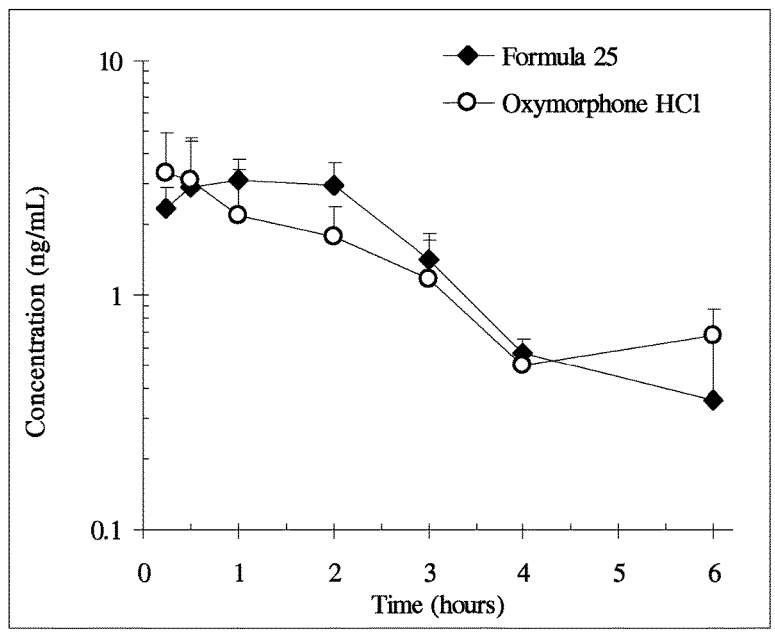
Fig 20: Rat oral PK profile of oxymorphone prodrug conjugate, Formula 30
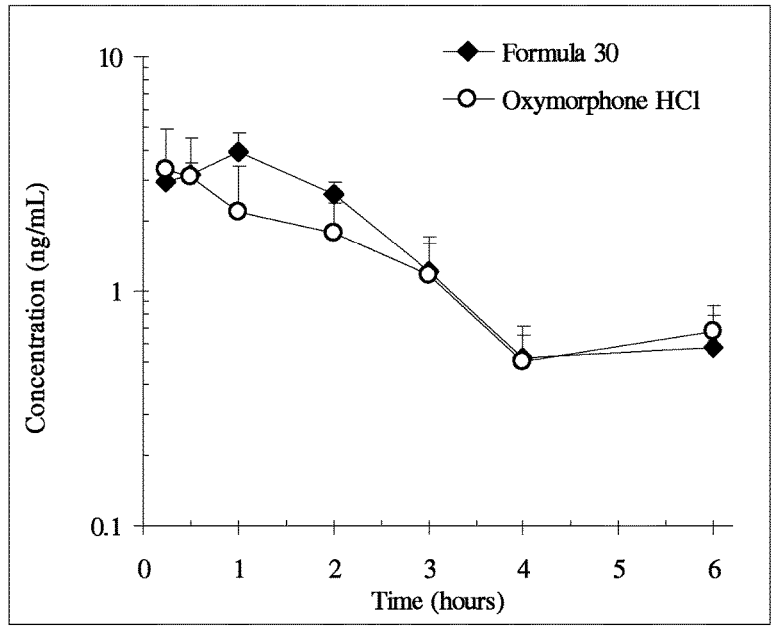

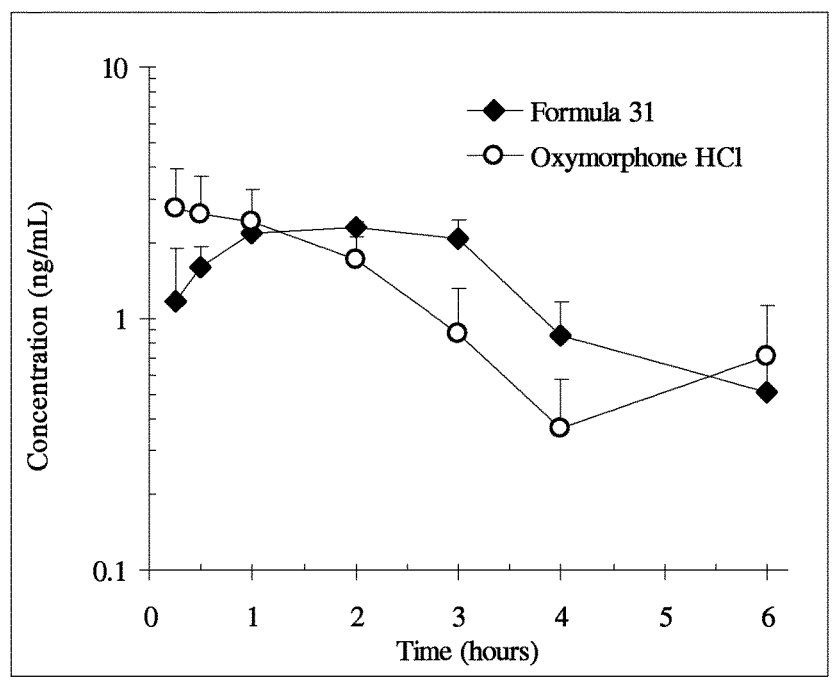
Fig 21: Rat oral PK profile of oxymorphone prodrug conjugate, Formula 31
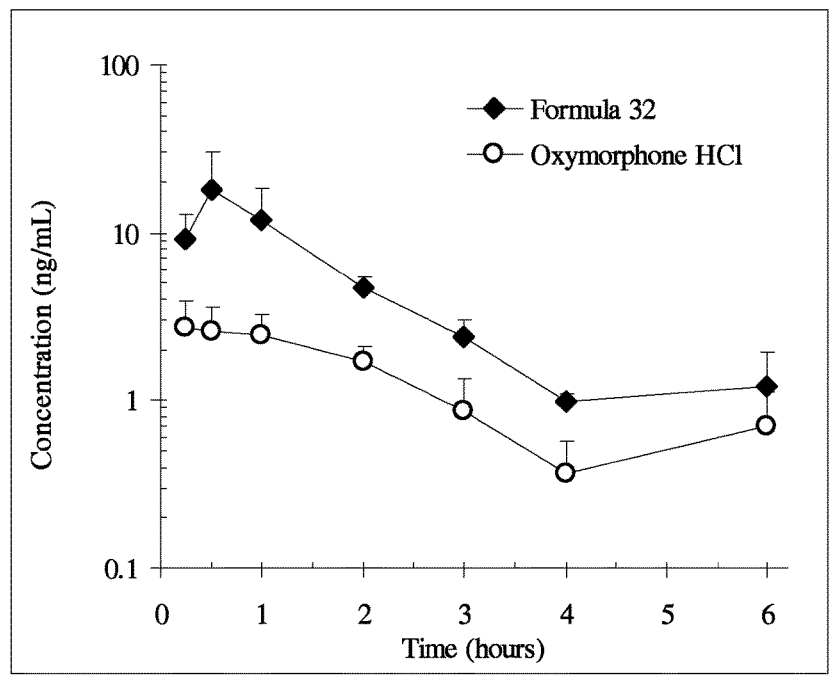
Fig 22: Rat oral PK profile of oxymorphone prodrug conjugate, Formula 32

Fig 23: Rat oral PK profile of oxymorphone prodrug conjugate, Formula 33
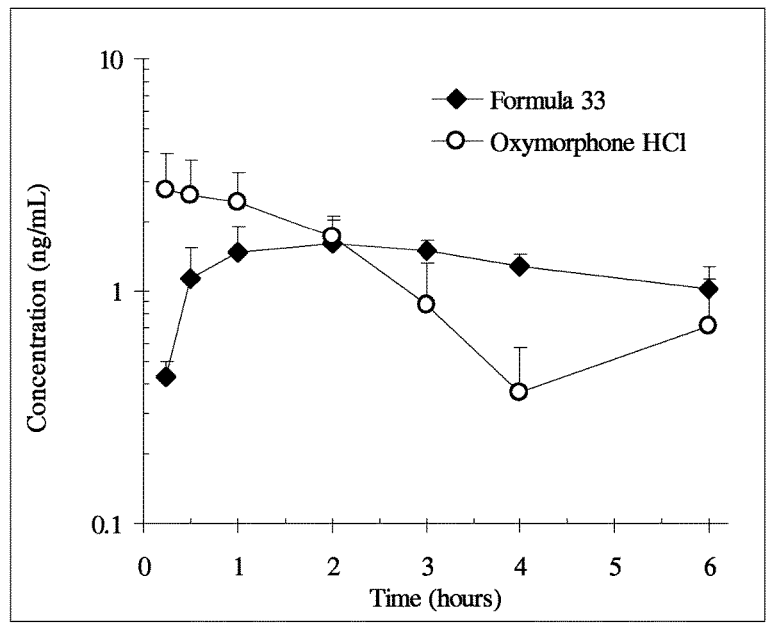
Fig 24: Rat oral PK profile of oxymorphone prodrug conjugate, Formula 34
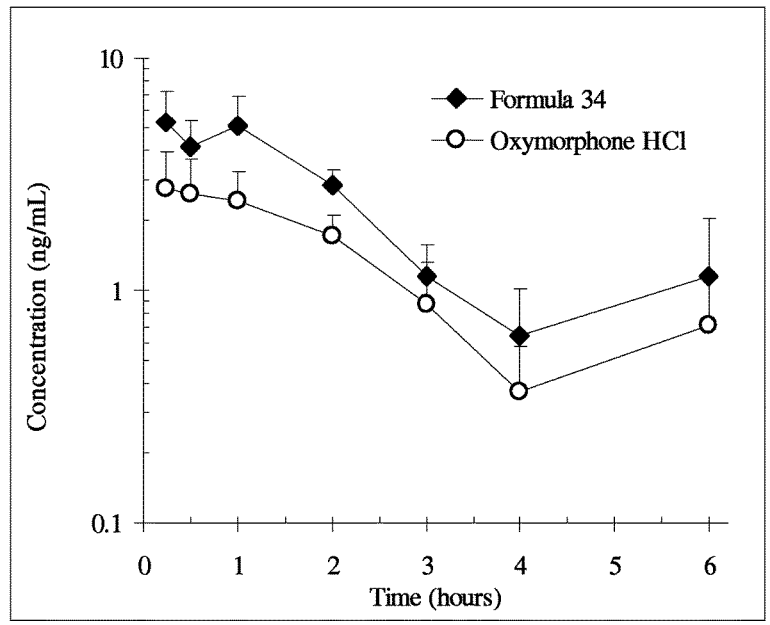

Fig 25: Rat oral PK profile of oxymorphone prodrug conjugate, Formula 39
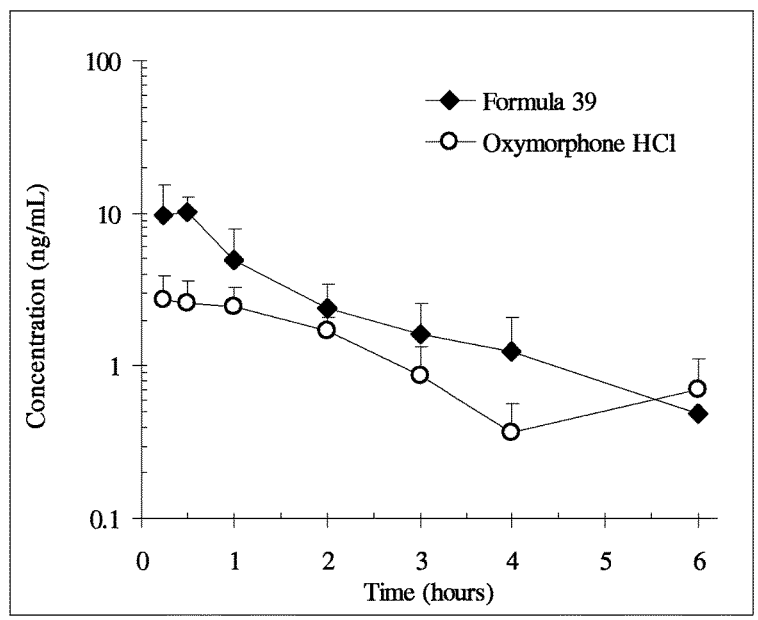
Fig 26: Rat oral PK profile of oxymorphone prodrug conjugate, Formula 40
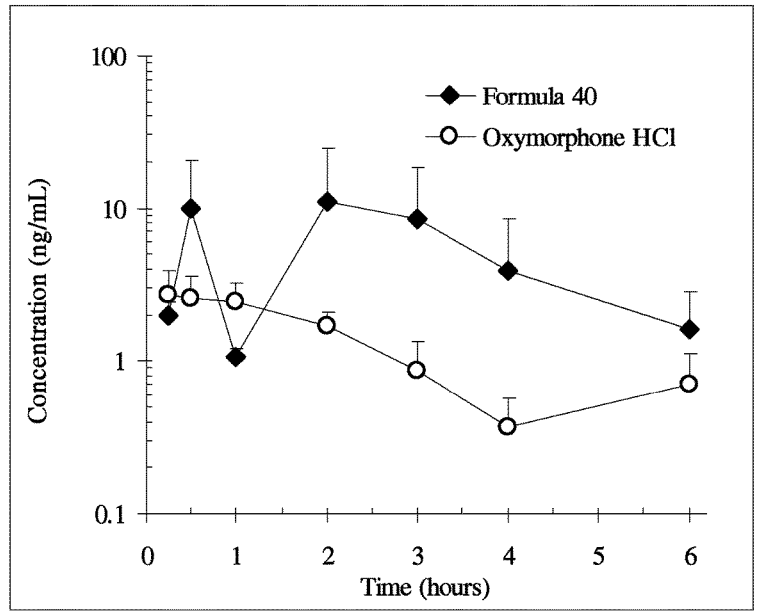

Fig 27: Rat oral PK profile of oxymorphone prodrug conjugate, Formula 41
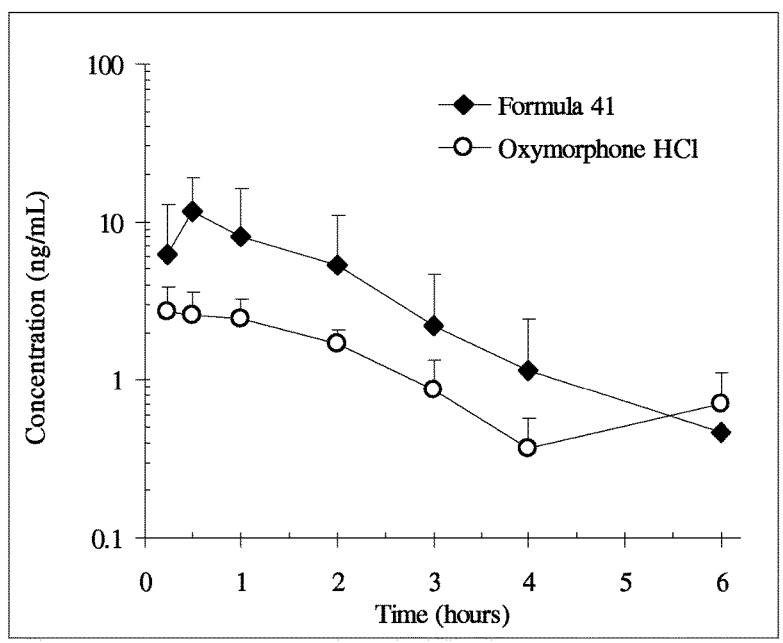
Fig 28: Rat oral PK profile of oxymorphone prodrug conjugate, Formula 42
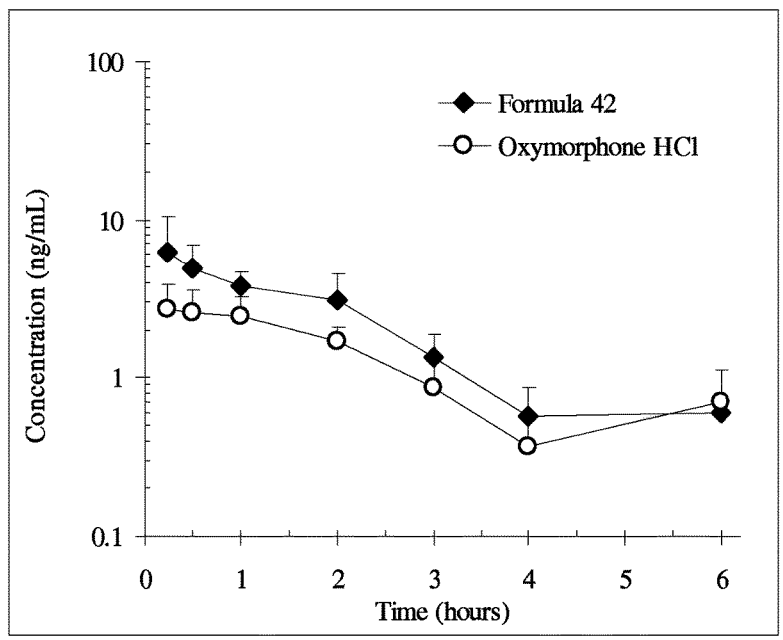

Fig 29: Rat oral PK profile of oxymorphone prodrug conjugate, Formula 43
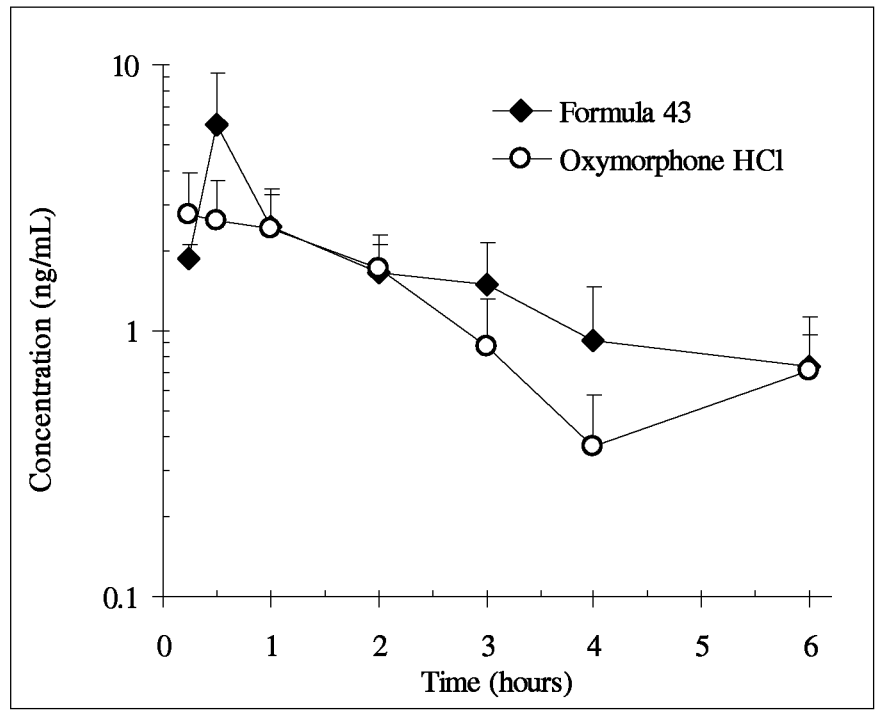
Fig 30: Rat oral PK profile of oxymorphone prodrug conjugate, Formula 46
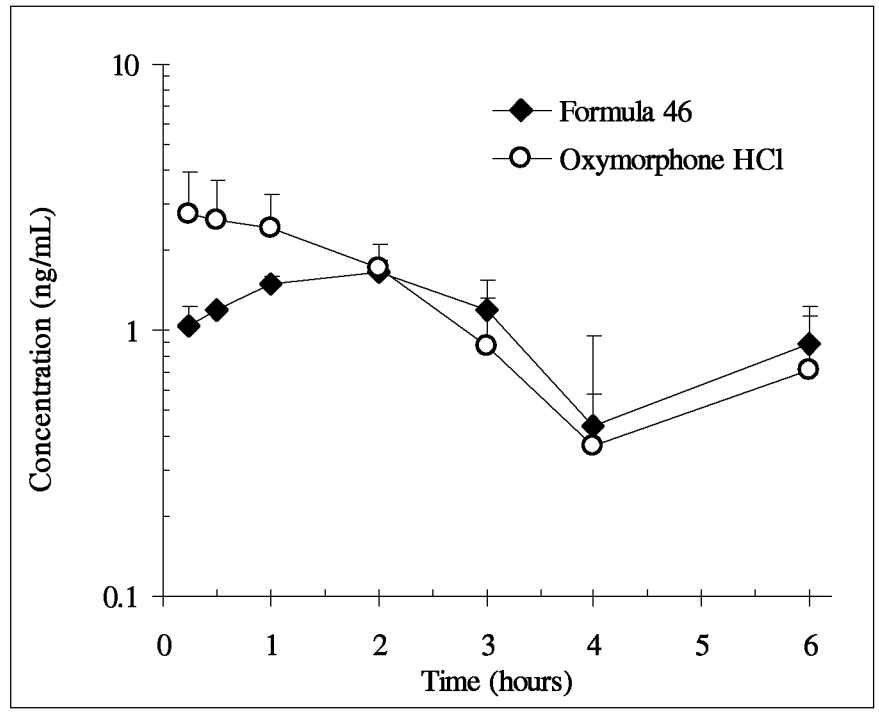

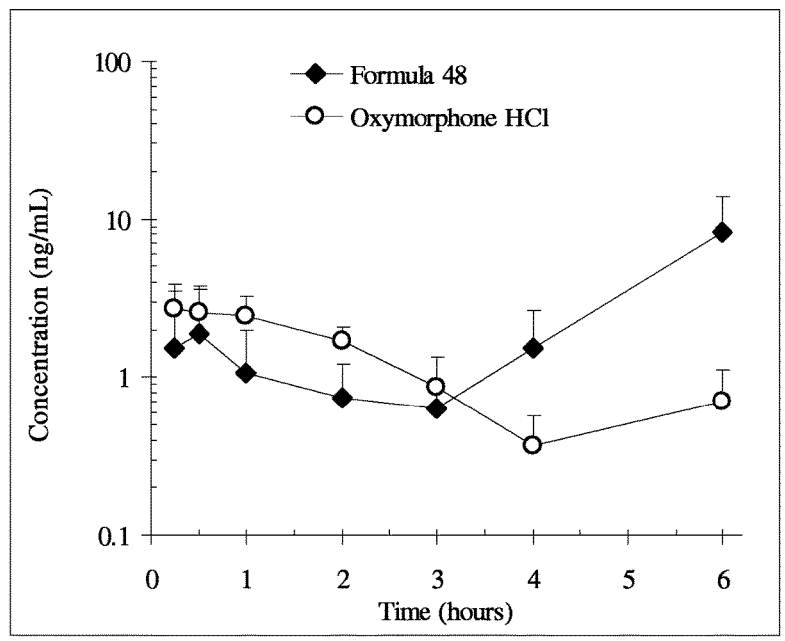
Fig 31: Rat oral PK profile of oxymorphone prodrug conjugate, Formula 48
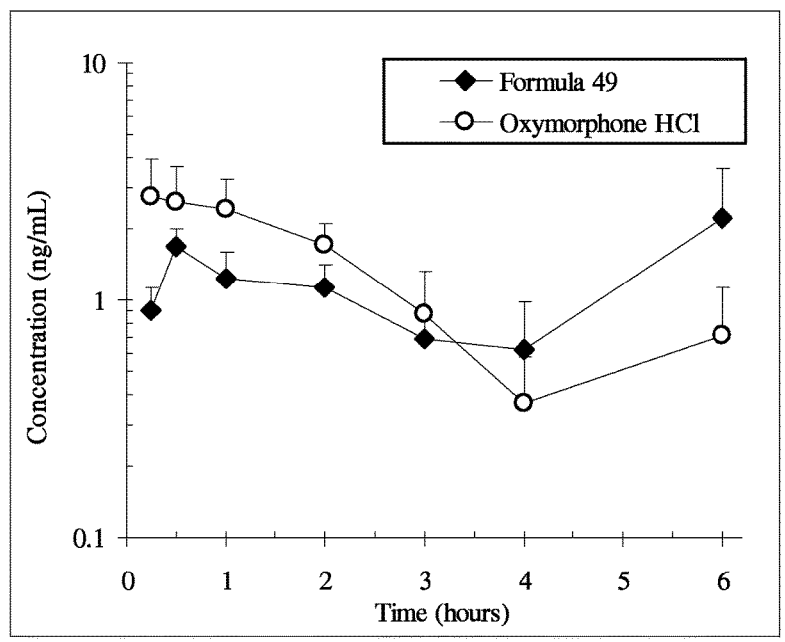
Fig 32: Rat oral PK profile of oxymorphone prodrug conjugate, Formula 49

Fig 33: Rat oral PK profile of oxymorphone prodrug conjugate, Formula 62
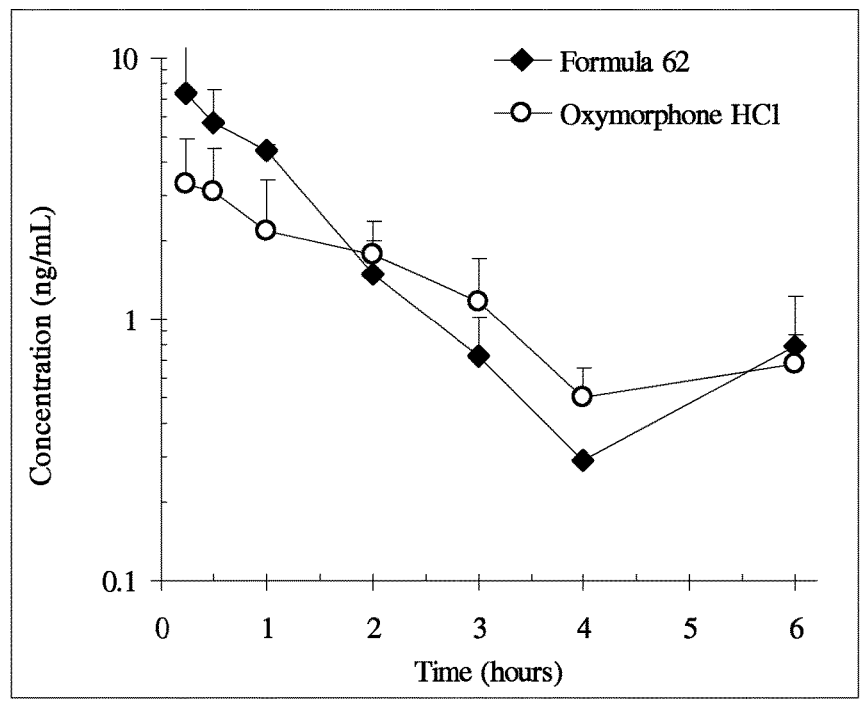
Fig 34: Rat oral PK profile of oxymorphone prodrug conjugate, Formula 64
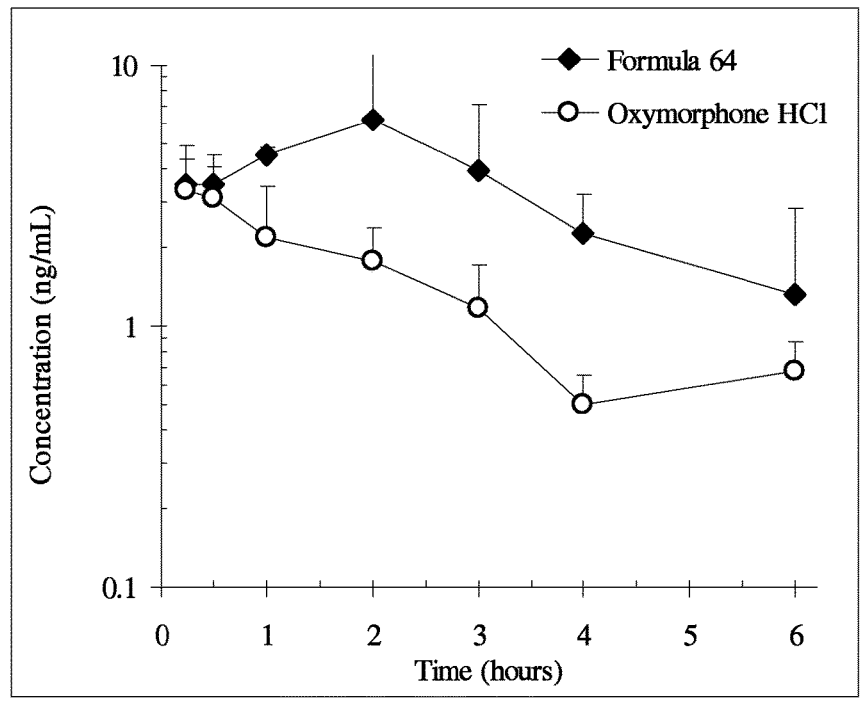

Fig 35: Rat oral PK profile of oxymorphone prodrug conjugate, Formula 65
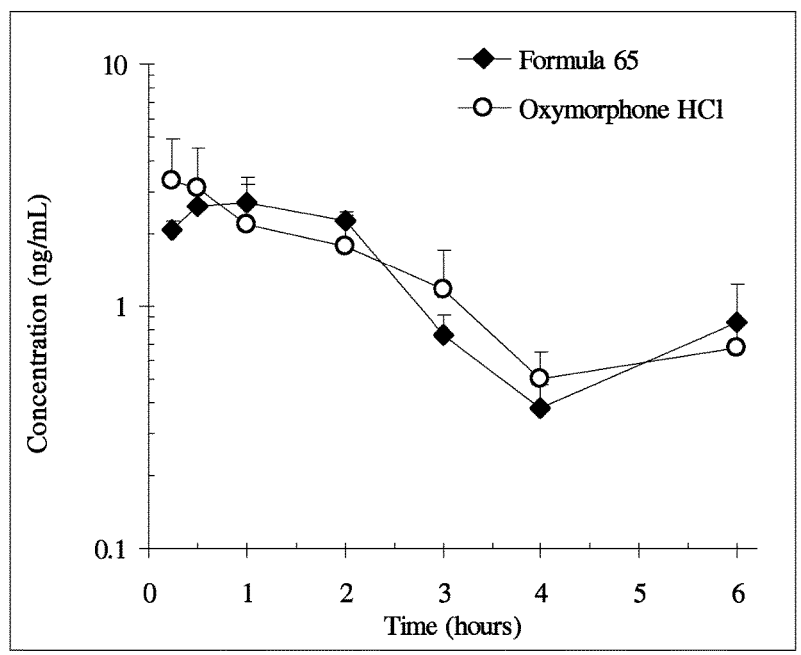
Fig 36: Rat oral PK profile of oxymorphone prodrug conjugate, Formula 66
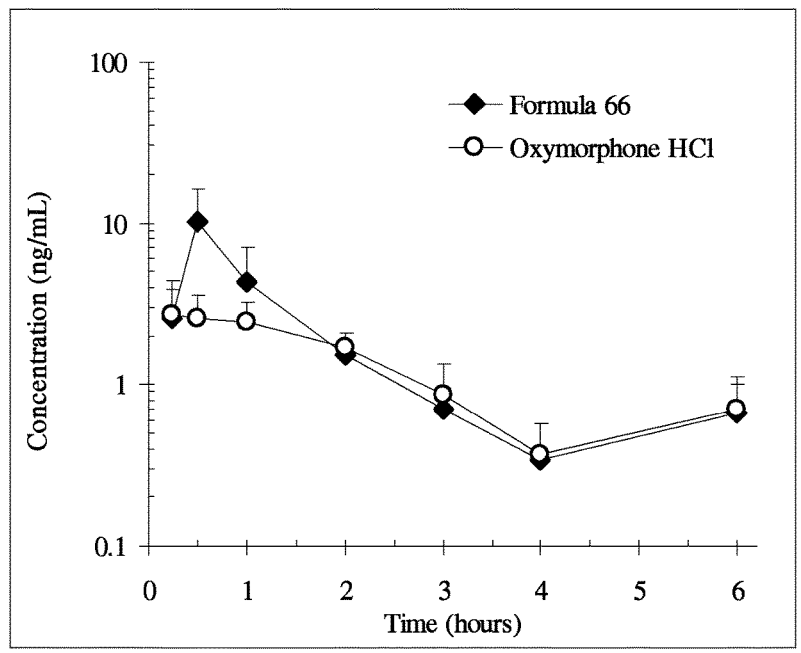

Fig 37: Rat oral PK profile of oxymorphone prodrug conjugate, Formula 67
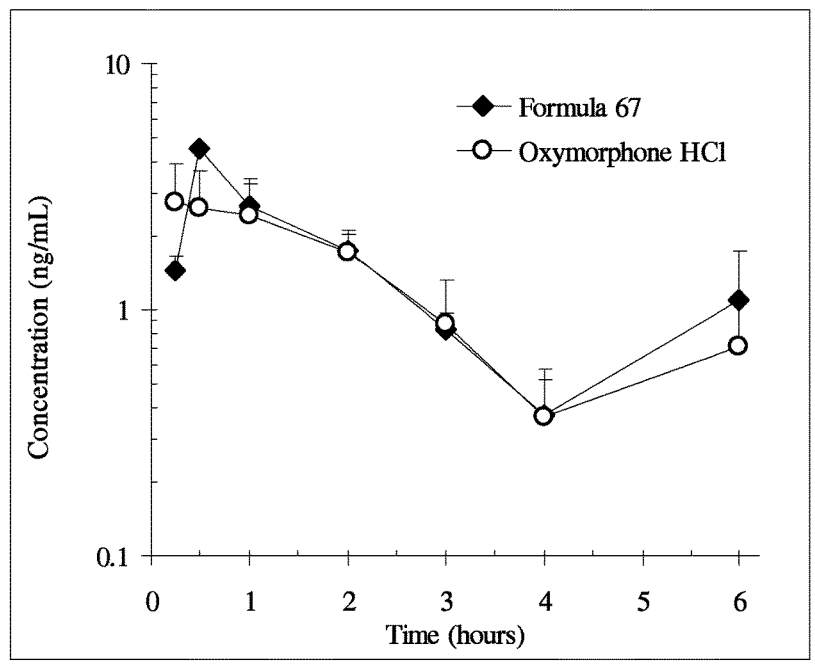
Fig 38: Rat oral PK profile of oxymorphone prodrug conjugate, Formula 69
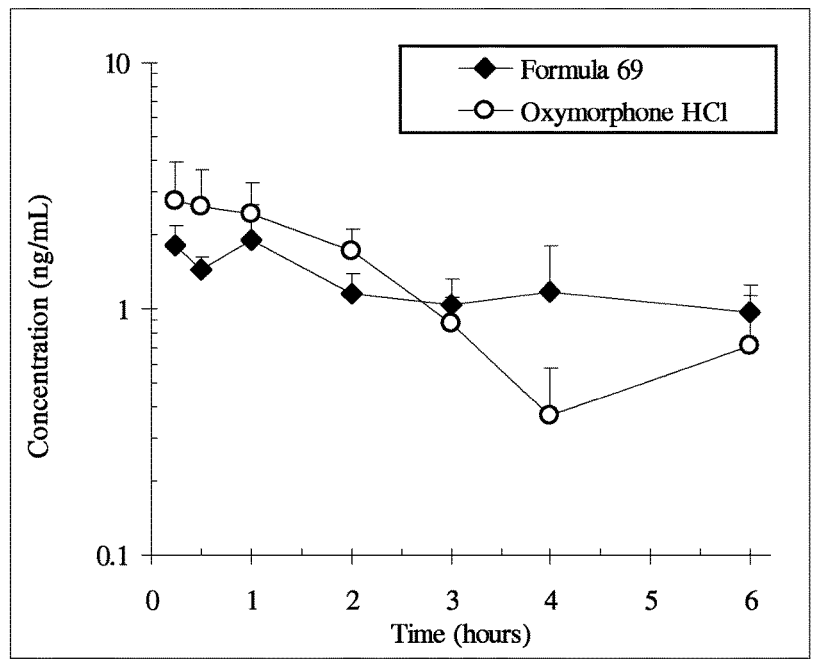

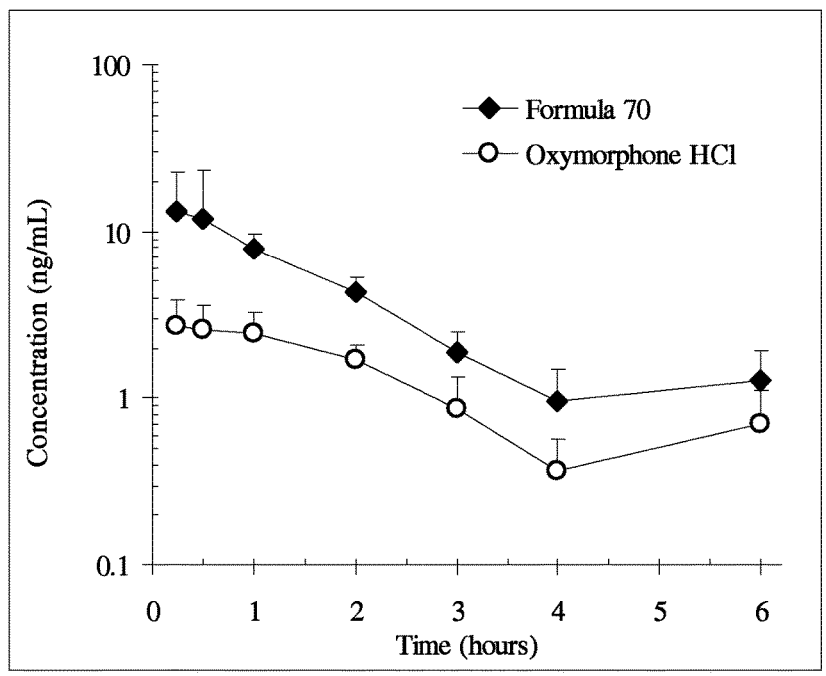
Fig 39: Rat oral PK profile of oxymorphone prodrug conjugate, Formula 70
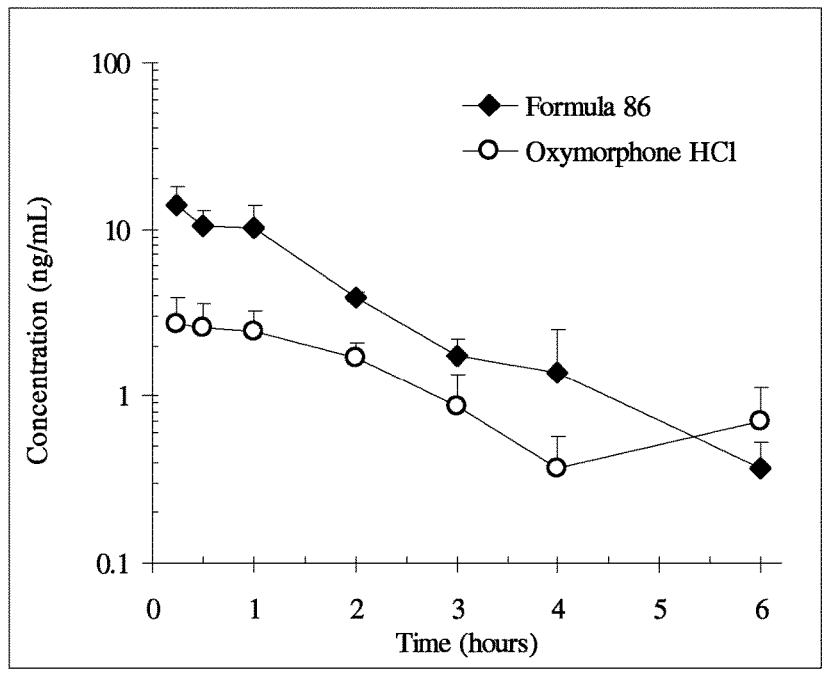
Fig 40: Rat oral PK profile of oxymorphone prodrug conjugate, Formula 86

Fig 41: Rat oral PK profile of oxymorphone prodrug conjugate, Formula 92
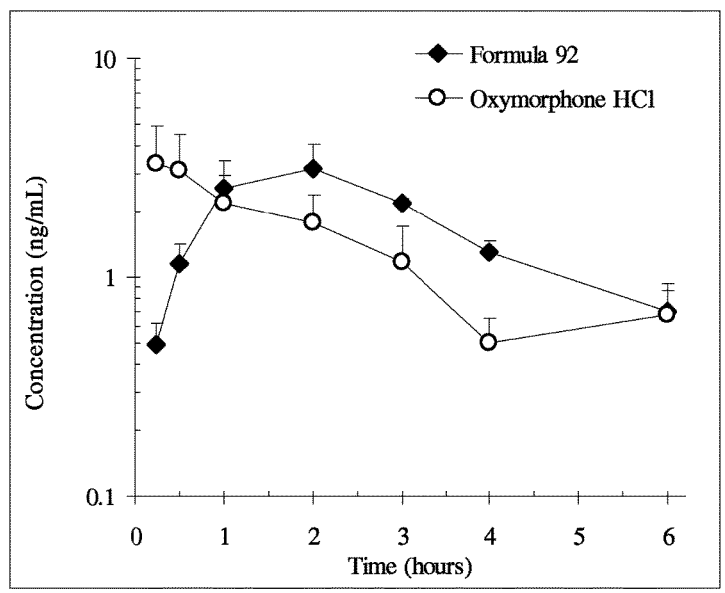
Fig 42: Rat oral PK profile of oxymorphone prodrug conjugate, Formula 93
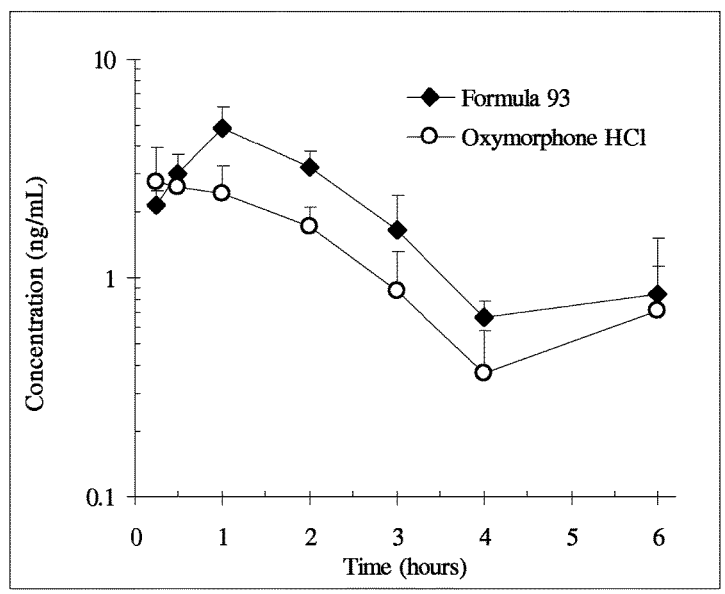

ALPHA-HYDROXY CARBOXYLIC ACID AND DERIVATIVES AND OTHER GRAS-BASED PRODRUGS OF OXYMORPHONE AND USES THEREOF

CROSS REFERENCE TO RELATED APPLICATIONS

This application claims priority to U.S. Provisional Application No. 62/153,157, filed on Apr. 27, 2015, the disclosure of which is incorporated by reference in its entirety.

FIELD OF INVENTION

The present invention relates to pharmaceutical compounds, compositions, and methods of using chemical moieties that are generally recognized as safe (GRAS) and that are attached to the opioid, oxymorphone. These chemical moieties are monomers, as well as homo- and hetero-oligomers, of alpha-hydroxy carboxylic acids and their chemical derivatives. These inventions provide a variety of beneficial effects, particularly a substantial decrease in the potential of oxymorphone to cause overdose or to be abused. Some embodiments of the invention provide therapeutic activity similar to that of unmodified oxymorphone at typical dosage; however, the risk of overdose from higher doses is reduced due to decreased bioavailability of oxymorphone. Overdose risk reduction is especially reduced if the drug would be taken by a non-approved route, as compared to non-conjugated oxymorphone administered by the approved oral route. Additionally, these prodrugs may be designed to provide fast or slow release of oxymorphone depending on its standard use for chronic or acute pain.

BACKGROUND OF THE INVENTION

Proper medical treatment of pain remains a challenge for patients and healthcare professionals. Optimal pharmacologic management of pain requires selection of analgesic drugs that achieve rapid efficacy with minimal side effects. Traditionally, opioid analgesics have provided the most important options for pain treatment. However, misuse and abuse of opioids are widespread social and medical problems that may deter physicians from prescribing these useful drugs.

In addition, accidental and intentional overdose with prescription and/or over-the-counter (OTC) drugs is a serious health problem that is associated with thousands of fatalities every year. Opioid overdose is a significant and growing problem associated with drug abuse, but overdoses also occur accidentally (e.g., when a child obtains and ingests an opioid), or intentionally (e.g., when related to suicide attempts). Accidental overdose can also commonly occur when unusually potent batches of illicit opioids are ingested by drug addicts or other abusers.

Opioid abuse is an increasing problem, and oxymorphone has become one of the most widely abused drugs. This opioid is also known as "a poor man's heroin" because of its comparatively lower street price. Moreover, crushing and intranasally snorting the extended release form of oxymorphone (known by the brand name as Opana-ER®), results in rapid drug release and absorption, which results in high peak blood concentrations that produce a quick "high" but can also precipitate a fatal overdose. Moreover, in March 2015, Austin, Ind. was the center of HIV outbreak caused by the use of oxymorphone as an injectable recreational drug. Oxymorphone as Opana® has various street names, such as "blues", "moons", "blue heaven", "pink lady", "Mrs. O", and others.

A further shortcoming of many opioids is their generally low oral bioavailability. Poor oral bioavailability results in variable blood levels, and consequently variable patient response—a highly undesirable feature in the treatment of pain where rapid and reliable relief is desired.

Researchers and the pharmaceutical industry have sought to prevent the potential harmful effects of opioid overdose by creation of various drug formulations. For example, opioids have been combined with opioid antagonists. Such formulations are designed to counteract an oral opioid if the formulation is disrupted (e.g., crushed) prior to oral administration, or if the drug is administered parenterally (e.g., intravenously). To cite an example of a non-opioid drug with known abuse potential, extended-release methylphenidate (Concerta®) has been formulated in a paste that can preclude administration by snorting or injection. Other compositions have been coated with emetic agents in quantities that, if administered in moderation as intended, no emesis occurs; however, if excessive amounts are ingested, emesis is induced to prevent overdose. However, such methods, as well as conventional controlled-release formulations, are often ineffective and can be circumvented.

In addition to oxymorphone hydrochloride, oxymorphone is also an ingredient of Opana® Injection (injectable), Opana® ER (extended-release tablet), Opana® IR (immediate-release tablet), Numorphan® (suppository and injectable solution), and O-Morphon® (both tablet and injectable). It is a semi synthetic narcotic analgesic derived from thebaine. Typical adult doses of oxymorphone range from 5-40 mg as the oral hydrochloride salt, whereas the injectable adult dose is approximately 1 mg as the hydrochloride salt, with a dosing interval ranging from 4-12 hours. Although typically used for the relief of moderate to moderately severe pain, oxymorphone can also produce drug dependence of the morphine type.

Various types of prodrugs have been proposed to improve the oral bioavailability of opioids. These have included simple ester conjugates that are subject to hydrolysis by plasma esterases. Moreover, the rapidity of ester hydrolysis within the gut or through first-pass metabolism in the liver has further limited the utility of this approach. More sophisticated ester-conjugated opioid prodrugs have been synthesized. However, in the 20 years since ester conjugates were first reported, no such prodrugs have been approved as marketed products, which suggest that this approach has not been successful.

Consequently, improved methods are urgently needed to make pharmaceutically effective oxymorphone compounds, along with compositions and methods of using such compounds, to reduce the potential for overdose and to reduce or deter opioid substance abuse while maintaining intended analgesic utility. Potentially useful compounds may also prevent or substantially diminish or delay uptake into the brain if the compounds were administered by routes other than approved oral administration.

Ideally, a prodrug moiety and its linkage to a particular opioid would be cleaved at an appropriate rate and site, which would then release the active opioid compound into the blood and provide the intended analgesic benefit. There remains a critical need for the treatment of severe pain with opioids using products that retain all their pharmacological advantages but sharply reduce their principal limitations, including adverse gastrointestinal effects (e.g., constipation), variable bioavailability after oral dosing, overdose, and misuse, illegal/illicit use and product tampering.

SUMMARY

Provided are pharmaceutical compounds, compositions, and methods of using such compounds and compositions. Also provided are methods of using chemical moieties that are generally recognized as safe (GRAS), which are attached to the opioid oxymorphone. These chemical moieties are monomers, homo- and hetero-oligomers of alpha-hydroxy carboxylic acids, and their chemical derivatives. The compounds may provide a substantial decrease in the potential of oxymorphone to cause overdose or to be abused. In some embodiments the oxymorphone prodrug conjugates provide therapeutic activity which is similar to that of unmodified oxymorphone when delivered at typical dosage ranges. However, when delivered at higher doses the potential for overdose is reduced as compared to conventional non-conjugated oxymorphone due to decreased bioavailability of the oxymorphone, especially when taken by non-approved oral routes. Additionally, the prodrugs may be designed to provide fast or slow release of oxymorphone depending on its standard use for chronic or acute pain.

BRIEF DESCRIPTION OF THE DRAWINGS

FIGS. 1-42 present the rat oral PK profiles of representative oxymorphone prodrug conjugates described herein. Oxymorphone HCl, 3.54 mg/kg was used as the reference and all the prodrug compounds weights were adjusted to 3.54 mg/kg oxymorphone HCl equivalent weight.

DETAILED DESCRIPTION OF THE INVENTION

A first aspect of the invention relates to changing the pharmacokinetic and pharmacological properties of oxymorphone through covalent modification using alpha-hydroxy carboxylic acid and derivatives and other generally recognized as safe (GRAS)-based moieties to produce prodrugs of oxymorphone. Covalent attachment of a chemical moiety—specifically, a moiety derived from alpha-hydroxy carboxylic acid and derivatives, as well as other GRAS-based reagents as monomers and oligomers (homo and hetero oligomers)—to oxymorphone may change one or more of the following properties of oxymorphone: the rate of absorption; extent of absorption and distribution within the body; metabolism and drug elimination (i.e., ADME pharmacokinetic properties). As such, the alteration of one or more of these characteristics may be designed to provide fast or slow release, depending on need for relief of chronic pain versus acute pain. Additionally, alteration of one or more of these characteristics may reduce the previously noted side-effects associated with oxymorphone. In turn, these alterations may diminish or deter abuse potential. The oligomers formed from alpha-hydroxy carboxylic acid and derivatives can be homo- and hetero-'mers' and can be both linear and branched 'mers'. The hetero 'mers' can be cross linked with other GRAS reagents. such as other alpha-hydroxy carboxylic acid, amino acid and dicarboxylic acids including, but not limited to, fumaric acid, maleic acid and succinic acid.

The oxymorphone prodrug may also prevent abuse by exhibiting stability under conditions that are likely to be employed by chemists who may illicitly attempt to release the oxymorphone compound from its attached group. The oxymorphone prodrug may further prevent abuse by exhibiting reduced bioavailability when administered via parenteral routes, particularly by intravenous, intranasal, or inhalation ("smoking") routes that are often employed in illicit use. Thus, the oxymorphone prodrug may reduce the desired euphoric effect associated with oxymorphone abuse, thereby preventing, deterring, or reducing abuse potential and overdose if the oxymorphone prodrug were to be used in an unapproved manner (e.g., ingestion of a higher dose or by non-oral administration).

Oxymorphone prodrugs of the present invention may be depicted as structures shown below as Formula A and Formula B where moieties X and Y represent the prodrug components that are chemically/covalently attached to oxymorphone at the $6^{th}$ and $14^{th}$ position oxygen atoms of oxymorphone, respectively, and both X and Y, if present, can be the same or different, or a pharmaceutically acceptable salt thereof. As shown in Formula A, if Y is not present the oxymorphone prodrug has a hydroxyl group at the $14^{th}$ position, and X may be any of the prodrug components described herein. As further described herein below, if both X and Y are present they may be the same or different, and each of X and Y may be independently selected from any of the prodrug components described.

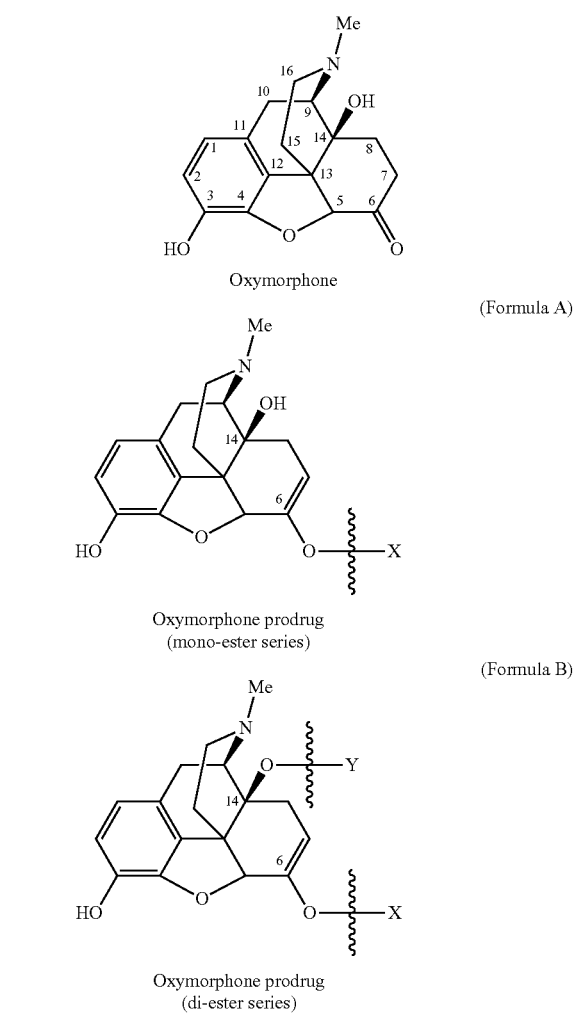

Alpha-hydroxy carboxylic acids and other GRAS-based monomers used to make the monomer-based and oligomer-based oxymorphone prodrugs are depicted below.

It should be emphasized that the following chemical moieties represent non-limiting examples of alpha-hydroxy carboxylic acids and other GRAS-based monomers used to make the monomer-based and oligomer-based oxymorphone prodrugs of the present invention:

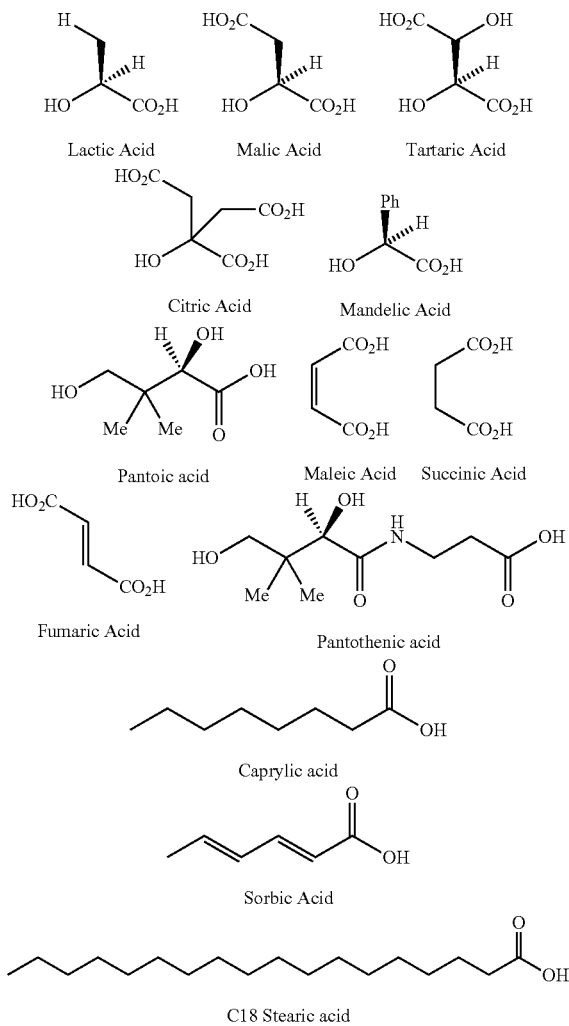

C8-C20 Fatty Acids; Palmitic acid, Linoleic acid, Oleic acid as examples
Amino Acids including Alpha, Beta, Gama and Epsilon amino acids The alpha-hydroxy carboxylic acids represented here include the naturally occurring (L)-isomers, the non-natural (D)-isomers, mixtures of (L) and (D) isomers, racemates and mixtures of diastereomers, and meso-isomers.

The amino acids represented here include both natural and non-natural amino acids, the naturally occurring (L)-isomers, the non-natural (D)-isomers, mixtures of (L) and (D) isomers, racemates and mixtures of diastereomers.

The amino acids represented here also include alpha amino acids, beta amino acids, gamma amino acids, and epsilon amino acids (i.e., amino group remote relative to the carboxyl group).

The fatty acids represented here include long-chain carboxylic acids, ranging in carbon lengths between eight carbons (C8) to twenty carbons (C20). These fatty acids could be both linear and branched and both saturated and non-saturated. In the case of unsaturated fatty acids, they could be both cis- and trans-isomers (Z and E isomers).

In one embodiment of the present invention, the prodrug components X and Y, if Y is present, may be the same or different and may be represented as,

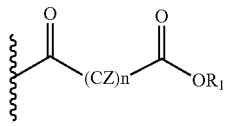

wherein,
$CZ=CH_2$, $CHOR_1$,
R1=H, acyl groups from fatty acids, acyl groups from alpha-hydroxy acids, acyl groups from amino acids, and acyl groups from dicarboxylic acids including, but not limited to, fumaric acid, maleic acid and succinic acid, and
R=Methyl (Me), Phenyl (Ph), $CH_2COR_2$, $CHOR_1COR_2$, and $COR_2$ (when n is not zero), where R2=OH, or is part of an ester formed by the hydroxyl group of another alpha-hydroxy acid or part of an amide formed by the amine group of an amino acid, and
n is an integer selected from 0 to 2.

In another embodiment of the present invention, the prodrug components X and Y, if Y is present, may be the same or different and may be represented as,

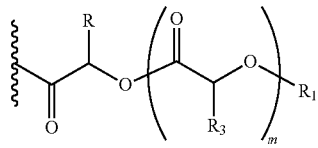

wherein,
R1=H, acyl groups from fatty acids, acyl groups from alpha-hydroxy acids and acyl groups from amino acids and acyl groups from dicarboxylic acids including, but not limited to, fumaric acid, maleic acid and succinic acid, and
R and R3 can be same or different, and
R and R3=Me, Ph, $CH_2COR_2$, $CHOR_1COR_2$, where R2=OH or is part of an ester formed by the hydroxyl group of another alpha-hydroxy acid or part of an amide formed by the amine group of an amino acid, and
m is an integer selected from 0 to 4.

In another embodiment of the present invention, the prodrug components X and Y, if Y is present, may be the same or different and may be represented as,

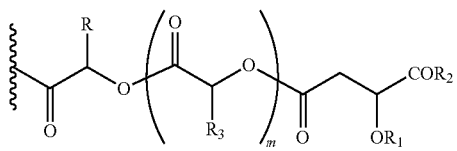

wherein,
R1=H, acyl groups from fatty acids, acyl groups from alpha-hydroxy acids and acyl groups from amino acids and acyl groups from dicarboxylic acids including, but not limited to, fumaric acid, maleic acid and succinic acid, and
R and R3 can be same or different, and R and R3=Me, Ph, CH2COR2, CHOR1COR2, where
R2=OH or is part of an ester formed by the hydroxyl
group of another alpha-hydroxy acid or part of an amide
formed by the amine group of an amino acid, and
m is an integer selected from 0 to 4.

In another embodiment of the present invention, the prodrug components X and Y, if Y is present, may be the same or different and may be represented as,

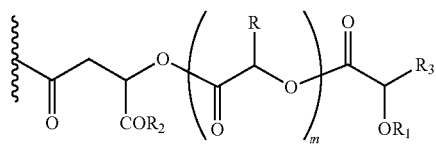

wherein,
R1=H, acyl groups from fatty acids, acyl groups from alpha-hydroxy acids and acyl groups from amino acids and acyl groups from dicarboxylic acids including, but not limited to, fumaric acid, maleic acid and succinic acid, and
R and R3 can be same or different, and
R and R3=Me, Ph, CH2COR2, CHOR1COR2, where R2=OH or is part of an ester formed by the hydroxyl group of another alpha-hydroxy acid or part of an amide formed by the amine group of an amino acid, and
m is an integer selected from 0 to 4.

In another embodiment of the present invention, the prodrug components X and Y, if Y is present, may be the same or different and may be represented as,

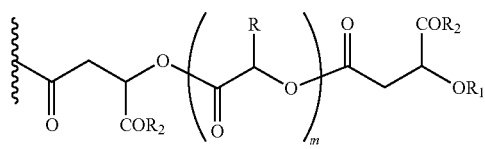

wherein,
R1=H, acyl groups from fatty acids, acyl groups from alpha-hydroxy acids and acyl groups from amino acids, and acyl groups from dicarboxylic acids including, but not limited to, fumaric acid, maleic acid and succinic acid, and
R=Me, Ph, CH2COR2, CHOR1COR2, where R2=OH or is part of an ester formed by the hydroxyl group of another alpha-hydroxy acid or part of an amide formed by the amine group of an amino acid, and
m is an integer selected from 0 to 4.

In another embodiment of the present invention, the prodrug components X and Y, if Y is present, may be the same or different and may be represented as,

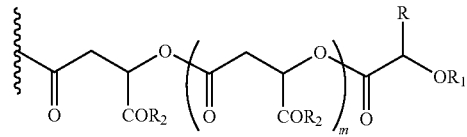

wherein,
R1=H, acyl groups from fatty acids, acyl groups from alpha-hydroxy acids and acyl groups from amino acids and acyl groups from dicarboxylic acids including, but not limited to, fumaric acid, maleic acid and succinic acid, and
R=Me, Ph, CH2COR2, CHOR1COR2, where R2=OH or is part of an ester formed by the hydroxyl group of another alpha-hydroxy acid or part of an amide formed by the amine group of an amino acid, and
m is an integer selected from 0 to 4.

In another embodiment of the present invention, the prodrug components X and Y, if Y is present, may be the same or different and may be represented as,

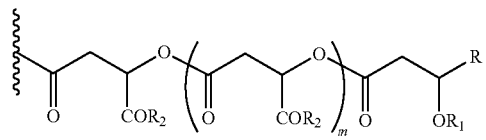

wherein,
R1=H, acyl groups from fatty acids, acyl groups from alpha-hydroxy acids and acyl groups from amino acids and acyl groups from dicarboxylic acids including, but not limited to, fumaric acid, maleic acid and succinic acid, and
R=Me, Ph, CH2COR2, CHOR1COR2, where R2=OH or is part of an ester formed by the hydroxyl group of another alpha-hydroxy acid or part of an amide formed by the amine group of an amino acid, and
m is an integer selected from 0 to 4.

In another embodiment of the present invention, the prodrug components X and Y, if Y is present, may be the same or different and may be represented as,

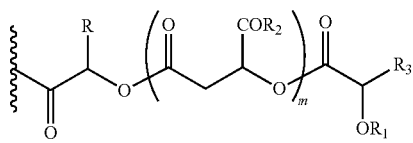

wherein,
R1=H, acyl groups from fatty acids, acyl groups from alpha-hydroxy acids and acyl groups from amino acids and acyl groups from dicarboxylic acids including, but not limited to, fumaric acid, maleic acid and succinic acid and
R and R3 can be same or different, and
R and R3=Me, Ph, CH2COR2, CHOR1COR2, where R2=OH or is part of an ester formed by the hydroxyl group of another alpha-hydroxy acid or part of an amide formed by the amine group of an amino acid, and
m is an integer selected from 0 to 4.

In another embodiment of the present invention, the prodrug components X and Y, if Y is present, may be the same or different and may be represented as,

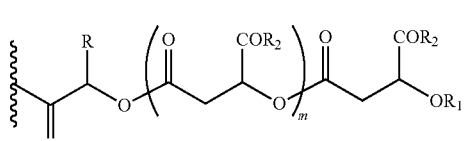

wherein,
R1=H, acyl groups from fatty acids, acyl groups from alpha-hydroxy acids and acyl groups from amino acids and acyl groups from dicarboxylic acids including, but not limited to, fumaric acid, maleic acid and succinic acid, and
R=Me, Ph, CH2COR2, CHOR1COR2, where R2=OH or is part of an ester formed by the hydroxyl group of another alpha-hydroxy acid or part of an amide formed by the amine group of an amino acid, and
m is an integer selected from 0 to 4

In another embodiment of the present invention, the prodrug components X and Y, if Y is present, may be the same or different and may be represented as,

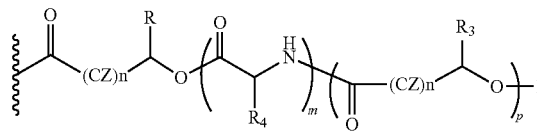

wherein,
CZ=CH2, CHOR1;
R1=H, acyl groups from fatty acids, acyl groups from alpha-hydroxy acids and acyl groups from amino acids and acyl groups from dicarboxylic acids including, but not limited to, fumaric acid, maleic acid and succinic acid, and
R and R3 can be same or different, and
R and R3=Me, Ph, CH2COR2, CHOR1COR2, where R2=OH or is part of an ester formed by the hydroxyl group of another alpha-hydroxy acid or part of an amide formed by the amine group of an amino acid, and
R4 together with the adjacent nitrogen atom is part of an amino acid, and the amino acids represented here depicts both natural and non-natural amino acids, the naturally occurring (L)-isomers, the non-natural (D)-isomers, mixtures of (L) and (D) isomers, racemates and mixtures of diastereomers, and
m is an integer selected from 0 to 4, and
n is an integer selected from 0 to 2, and
p is an integer selected from 0 to 1.

In another embodiment of the present invention, the prodrug components X and Y, if Y is present, may be the same or different and may be represented as,

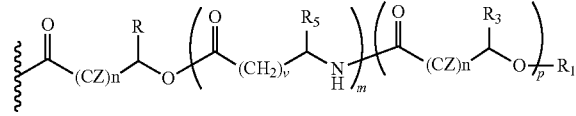

wherein,
CZ=CH2, CHOR1;
R1=H, acyl groups from fatty acids, acyl groups from alpha-hydroxy acids and acyl groups from amino acids, and acyl groups from dicarboxylic acids including, but not limited to, fumaric acid, maleic acid and succinic acid, and
R and R3 can be same or different, and
R and R3=Me, Ph, CH2COR2, CHOR1COR2, where R2=OH or is part of an ester formed by the hydroxyl group of another alpha-hydroxy acid or part of an amide formed by the amine group of an amino acid, and R5=H, COR2, where R2=OH or is part of an ester formed by the hydroxyl group of another alpha-hydroxy acid or part of an amide formed by the amine group of an amino acid, or alkyl esters (O-alkyl, alkyl group is 1-4 carbon linear and branched, saturated and non-saturated alkyl groups), and
the amino acids represented here depicts both natural and non-natural amino acids, the naturally occurring (L)-isomers, the non-natural (D)-isomers, mixtures of (L) and (D) isomers, racemates and mixtures of diastereomers, and
m is an integer selected from 0 to 4, and
n is an integer selected from 0 to 2, and
p is an integer selected from 0 to 1, and
v is an integer selected from 0 to 5.

In another embodiment of the present invention, the prodrug components X and Y, if Y is present, may be the same or different and may be represented as,

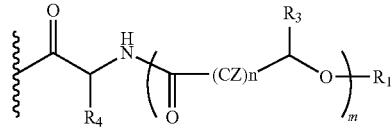

wherein,
CZ=CH2, CHOR1;
R1=H, acyl groups from fatty acids, acyl groups from alpha-hydroxy acids and acyl groups from amino acids and acyl groups from dicarboxylic acids including, but not limited to, fumaric acid, maleic acid and succinic acid, and
R3=Me, Ph, CH2COR2, CHOR1COR2, where R2=OH or is part of an ester formed by the hydroxyl group of another alpha-hydroxy acid or part of an amide formed by the amine group of an amino acid, and the amino acids represented here depicts both natural and non-natural amino acids, the naturally occurring (L)-isomers, the non-natural (D)-isomers, mixtures of (L) and (D) isomers, racemates and mixtures of diastereomers, and
R4 together with the adjacent nitrogen atom is part of an amino acid and the amino acids represented here depicts both natural and non-natural amino acids, the naturally occurring (L)-isomers, the non-natural (D)-isomers, mixtures of (L) and (D) isomers, racemates and mixtures of diastereomers, and
m is an integer selected from 0 to 4, and
n is an integer selected from 0 to 2, In another embodiment of the present invention, the prodrug components X and Y, if Y is present, may be the same or different and may be represented as,

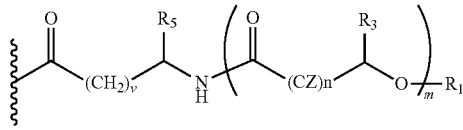

wherein,
CZ=CH2, CHOR1;
R1=H, acyl groups from fatty acids, acyl groups from alpha-hydroxy acids and acyl groups from amino acids and acyl groups from dicarboxylic acids including, but not limited to, fumaric acid, maleic acid and succinic acid, and R3=Me, Ph, CH2COR2, CHOR1COR2, where R2=OH or is part of an ester formed by the hydroxyl group of another alpha-hydroxy acid or part of an amide formed by the amine group of an amino acid, and the amino acids represented here depicts both natural and non-natural amino acids, the naturally occurring (L)-isomers, the non-natural (D)-isomers, mixtures of (L) and (D) isomers, racemates and mixtures of diastereomers, and R5=H, COR2, where R2=OH or is part of an ester formed by the hydroxyl group of another alpha-hydroxy acid or part of an amide formed by the amine group of an amino acid, or alkyl esters (O-alkyl, alkyl group is 1-4 carbon linear and branched, saturated and non-saturated alkyl groups), and the amino acids represented here depicts both natural and non-natural amino acids, the naturally occurring (L)-isomers, the non-natural (D)-isomers, mixtures of (L) and (D) isomers, racemates and mixtures of diastereomers, and m is an integer selected from 0 to 4, and n is an integer selected from 0 to 2, and v is an integer selected from 0 to 5.

In another embodiment of the present invention, the prodrug components X and Y, if Y is present, may be the same or different and may be represented as,

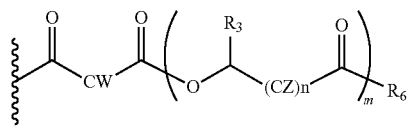

wherein,

CW=(CH2)q, CH=CH (both E and Z isomers),

CZ=CH2, CHOR1;

R1=H, acyl groups from fatty acids, acyl groups from alpha-hydroxy acids and acyl groups from amino acids and acyl groups from dicarboxylic acids including, but not limited to, fumaric acid, maleic acid and succinic acid, and R3=Me, Ph, CH2COR2, CHOR1COR2, where R2=OH or is part of an ester formed by the hydroxyl group of another alpha-hydroxy acid or part of an amide formed by the amine group of an amino acid, and the amino acids represented here depicts both natural and non-natural amino acids, the naturally occurring (L)-isomers, the non-natural (D)-isomers, mixtures of (L) and (D) isomers, racemates and mixtures of diastereomers, and R6=OH or is part of an ester formed by the hydroxyl group of another alpha-hydroxy acid or part of an amide formed by the amine group of an amino acid, or alkyl esters (O-alkyl, alkyl group is 1-4 carbon linear and branched, saturated and non-saturated alkyl groups), and, the amino acids represented here depicts both natural and non-natural amino acids, the naturally occurring (L)-isomers, the non-natural (D)-isomers, mixtures of (L) and (D) isomers, racemates and mixtures of diastereomers, and m is an integer selected from 0 to 4, and n is an integer selected from 0 to 2, and q is an integer selected from 2 to 6.

In another embodiment of the present invention, the prodrug components X and Y, if Y is present, may be the same or different and may be represented as,

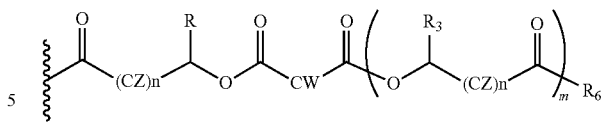

wherein,

CW=(CH2)q, CH=CH (both E and Z isomers),

CZ=CH2, CHOR1;

R1=H, acyl groups from fatty acids, acyl groups from alpha-hydroxy acids and acyl groups from amino acids, and acyl groups from dicarboxylic acids including, but not limited to, fumaric acid, maleic acid and succinic acid, and R and R3 can be same or different, and R and R3=Me, Ph, CH2COR2, CHOR1COR2, where R2=OH or is part of an ester formed by the hydroxyl group of another alpha-hydroxy acid or part of an amide formed by the amine group of an amino acid, and the amino acids represented here depicts both natural and non-natural amino acids, the naturally occurring (L)-isomers, the non-natural (D)-isomers, mixtures of (L) and (D) isomers, racemates and mixtures of diastereomers, and R6=OH or is part of an ester formed by the hydroxyl group of another alpha-hydroxy acid or part of an amide formed by the amine group of an amino acid, or alkyl esters (O-alkyl, alkyl group is 1-4 carbon linear and branched, saturated and non-non-saturated alkyl groups), and the amino acids represented here depicts both natural and non-non-natural amino acids, the naturally occurring (L)-isomers, the non-natural (D)-isomers, mixtures of (L) and (D) isomers, racemates and mixtures of diastereomers, and m is an integer selected from 0 to 4, and n is an integer selected from 0 to 2, and q is an integer selected from 2 to 6.

In another embodiment of the present invention, the prodrug components X and Y, if Y is present, may be the same or different and may be represented as,

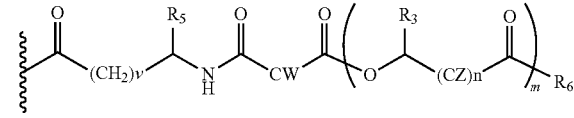

wherein,

CW=(CH2)q, CH=CH, (both E and Z isomers), and

R3=Me, Ph, CH2COR2, CHOR1COR2, where R2=OH or is part of an ester formed by the hydroxyl group of another alpha-hydroxy acid or part of an amide formed by the amine group of an amino acid, and the amino acids represented here depicts both natural and non-non-natural amino acids, the naturally occurring (L)-isomers, the non-natural (D)-isomers, mixtures of (L) and (D) isomers, racemates and mixtures of diastereomers, R5=H, COR2, where R2=OH or is part of an ester formed by the hydroxyl group of another alpha-hydroxy acid or part of an amide formed by the amine group of an amino acid, or alkyl esters (O-alkyl, alkyl group is 1-4 carbon linear and branched, saturated and non-non-saturated alkyl groups), and, R6=OH or is part of an ester formed by the alcohol (OH) part of another alpha-hydroxy acid or part of an amide formed by the amine group of an amino acid, or alkyl esters (O-alkyl, alkyl group is 1-4 carbon linear and branched, saturated and non-non-saturated alkyl groups), and, m is an integer selected from 0 to 4, and
n is an integer selected from 0 to 2, and
q is an integer selected from 2 to 6, and
v is an integer selected from 0 to 6.

In another embodiment of the present invention, the prodrug components X and Y, if Y is present, may be the same or different and may be represented as,

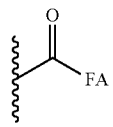

wherein,
FA is C8 to C20 saturated and unsaturated fatty acids including sorbic acid, stearic acid, oleic acid, palmitic acid, linoleic acid.
These fatty acids may be linear or branched chain acids, or a combination thereof;
and in the case of unsaturated fatty acids, they may be cis- or trans-isomers (Z and E isomers).

In another embodiment of the present invention, the prodrug side chain is attached to (i.e., bonded to) one of two (or both) possible locations in the oxymorphone molecule. For example, oxymorphone has hydroxyl groups at carbon 14 and a ketone oxygen at carbon 6. A monomer prodrug side-chain or an oligomer prodrug side-chain can be bound at either or both of these positions, and upon prodrug side-chain cleavage, the oxymorphone will revert back to its original form.

With the ketone group present at the 6 position of oxymorphone, the ketone can be converted to its corresponding enolate and reacted with an activated prodrug side chain to form a prodrug. Upon prodrug cleavage, the prodrug will revert back to the original opioid molecule with the keto group present.

If the prodrug chain is attached only to the ketone enolate oxygen at the 6 position of oxymorphone, it is the prodrug ester of the mono-series (mono-substitution), and if the prodrug chain is attached to both at the hydroxyl groups at carbon 14 and at the ketone enolate oxygen at the 6 position of oxymorphone, it is the prodrug ester of the bis-series (di-substitution). Upon cleavage of the prodrug side-chains, the prodrug will revert back to the original oxymorphone molecule, with the keto group and hydroxyl group present and intact.

The alpha-hydroxy carboxylic acid and its homo and hetero oligomers (with another alpha-hydroxy carboxylic acid) referred to in this invention should be understood to be covalently bound via a hydroxy group on the alpha-hydroxy carboxylic acid or on the oligomer to another carbonyl (originally part of a carboxyl group of another alpha-hydroxy carboxylic acid, or to another carbonyl of the carboxyl group of the amino acid, or to one carbonyl of the carboxyl group of a dicarboxylic acid (e.g., succinic acid, maleic acid, fumaric acid), while the carboxyl group from the initial alpha-hydroxy carboxylic acid is attached to oxymorphone.

If the initial carboxyl group that is attached to the oxymorphone referred to in this invention is from an amino acid, it should be understood that the amino group of the said amino acid is to be bound via a covalent bond as the amide with the carboxyl group on the alpha-hydroxy carboxylic acid or the oligomer carbonyl (originally part of a carboxyl group of the alpha-hydroxy carboxylic acids) or to one carbonyl of the carboxyl group of a dicarboxylic acid (e.g., succinic acid, maleic acid, fumaric acid).

It should also be understood that If the initial carboxyl group that is attached to the oxymorphone referred to in this invention is from alpha-hydroxy carboxylic acids and its homo and hetero oligomers (with another alpha-hydroxy carboxylic acid), the ensuing hydroxyl group may be capped as its ester by fatty acids.

It should also be understood that If the initial carboxyl group that is attached to the oxymorphone referred to in this invention is from alpha-hydroxy carboxylic acids and its homo and hetero oligomers (with another alpha-hydroxy carboxylic acid), the ensuing hydroxyl group may be capped as its ester by dicarboxylic acids (e.g., succinic acid, maleic acid, fumaric acid).

In another embodiment of the present invention, when the covalently modified oxymorphone is provided in oral dosage form (e.g., a tablet, capsule, caplet, liquid dispersion, etc.) it has increased resistance to manipulation. For instance, crushing of a tablet or disruption of a capsule does not substantially increase the rate and amount of oxymorphone absorbed when compositions of the invention are ingested.

In another embodiment of the present invention, when the oxymorphone covalently bound to the prodrug side chain is provided in oral dosage form: for example a tablet, capsule, caplet or other formulation that is resistant to release of oxymorphone by physical manipulation such as crushing.

Another embodiment of the present invention provides oxymorphone prodrug conjugates as a composition or method for treating pain in a patient (i.e., acute and chronic pain). It should be noted that different conjugates maybe be utilized to treat acute versus chronic pain.

Another embodiment of the present invention is a composition or method for a sustained-release oxymorphone comprising a covalently bonded oxymorphone conjugate, wherein said conjugate provides release of oxymorphone at a rate where the level of oxymorphone is within the therapeutic range, but below toxic levels, over an extended period of time (e.g., 8-24 hours or greater).

Another embodiment of the present invention is a composition or method for reducing variability in bioavailability, or preventing a toxic release of oxymorphone, comprising oxymorphone covalently bonded to the prodrug moiety, wherein said bound oxymorphone maintains a steady-state plasma release curve, which provides therapeutically effective bioavailability but prevents spikes or sharp increases in blood concentrations compared to unbound oxymorphone when given at doses exceeding those that are within the therapeutic range of oxymorphone.

Another embodiment of the invention is a composition or method for preventing an extreme spike in plasma $C_{max}$ for oxymorphone while still providing therapeutically effective bioavailability for oxymorphone that has been covalently bonded to the prodrug moiety.

Another embodiment of the present invention is a method for reducing or preventing abuse related to the euphoric effect of a pharmaceutical opioid composition, comprising consuming said composition, wherein said composition comprises a prodrug moiety covalently attached to oxymorphone, such that the pharmacological activity of oxymorphone is substantially decreased when the composition is used in a manner inconsistent with approved instructions or in a manner that substantially increases the potential of overdose.

Other embodiments of the present invention are methods wherein said pharmaceutical composition is adapted solely for oral administration, and wherein said oxymorphone is resistant to release from said prodrug moiety when the composition is administered parenterally (e.g., intranasally. intravenously. etc.). Preferably, said oxymorphone would be preferentially released from said chemical moiety primarily in the presence of acid and/or enzymes present in the stomach or intestinal tract, respectively.

In another embodiment of the present invention, the covalently bonded oxymorphone prodrug may also be in a pharmaceutically acceptable salt form. Pharmaceutically acceptable inorganic and organic acid addition salts are known in the art. Exemplary salts include, but are not limited to, hydrobromide, hydrochloride, hydroiodide, benzoate, bisulfate, tartrate, bitartrate, edetate, edisylate, estolate, esylate, ethanesulfonate, lactate, malate, maleate, mandelate, methanesulfonate, phosphate, 2-hydroxyethanesulfonate, 2-naphthalenesulfonate, 3-hydroxy-2-naphthoate, 3-phenylpropionate, acetate, adipate, alginate, amsonate, aspartate, benzenesulfonate, borate, butyrate, calcium edetate, camphorate, camphorsulfonate, citrate, clavulariate, cyclopentanepropionate, digluconate, dodecylsulfate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydroxynaphthoate, isothionate, lactobionate, laurate, laurylsulphonate, mucate, naphthylate, napsylate, nicotinate, N-methylglucamine ammonium salt, oleate, palmitate, pamoate, pantothenate, pectinate, phosphateldiphosphate, pivalate, polygalacturonate, propionate, p-toluenesulfonate, saccharate, salicylate, stearate, subacetate, succinate, sulfate, sulfosaliculate, suramate, tannate, teoclate, tosylate, triethiodide, undecanoate, and valerate salts, and the like.

The term "amino acid" refers to one of twenty-two amino acids used for protein biosynthesis, as well as other amino acids that can be incorporated into proteins during translation. Such amino acids can be a natural amino acid, such as glycine, alanine, valine, leucine, isoleucine, aspartic acid, glutamic acid, serine, threonine, glutamine, asparagine, arginine, lysine, proline, phenylalanine, tyrosine, tryptophan, cysteine, methionine, histidine and beta alanine, or non-natural amino acids and alpha amino acids, beta amino acids, gamma amino acids, and epsilon amino acids (e.g., the amino group is remote relative to the carboxyl group).

The present invention also provides methods for providing, administering, prescribing, or consuming an oxymorphone prodrug. The invention also provides pharmaceutical compositions comprising an oxymorphone prodrug. The formulation of such a pharmaceutical composition can optionally enhance or achieve the desired release profile.

In a further embodiment of the present invention, non-limiting examples of oxymorphone prodrugs of the present invention are shown in Formulae 1-93. In these formulae, it should be noted that while no salt forms have been depicted, all the formulae compounds can be prepared as their pharmaceutically acceptable salts, as previously described.

Non-limiting examples of oxymorphone prodrugs (formulae 1-93):

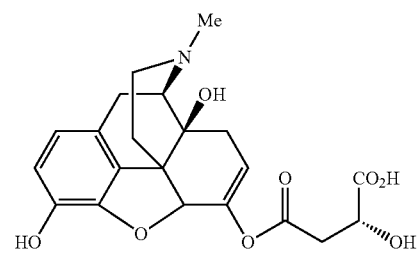

Formula 1

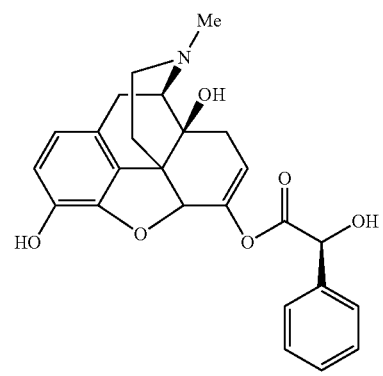

Formula 2

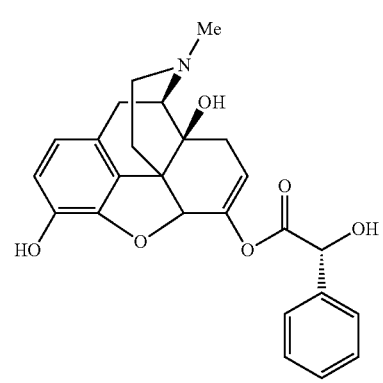

Formula 3

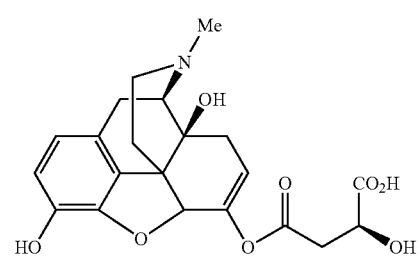

Formula 4

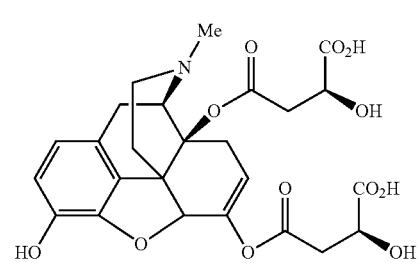

Formula 5

Formula 6
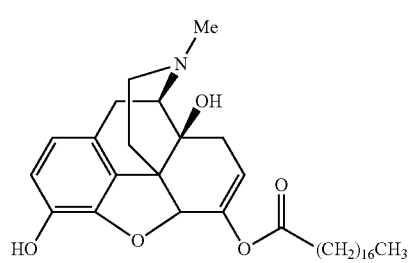
Formula 7
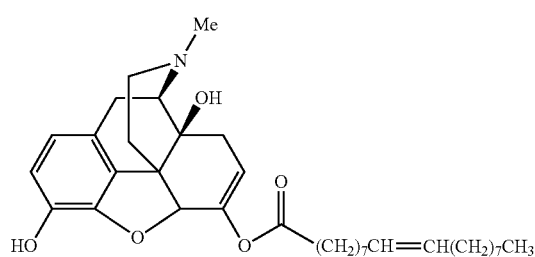
Formula 8
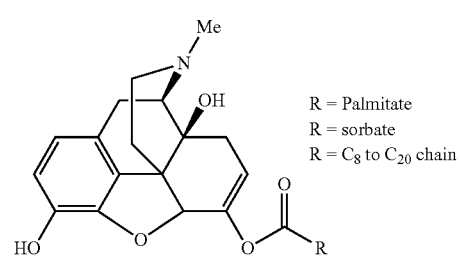
R = Palmitate
R = sorbate
R = $C_8$ to $C_{20}$ chain
Formula 9
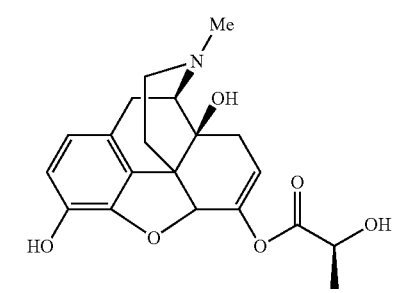
Formula 10
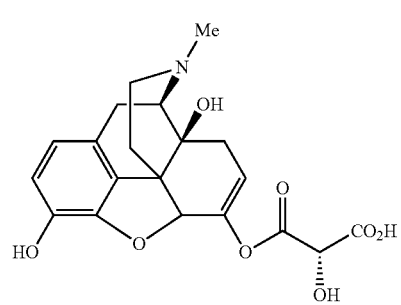
Formula 11
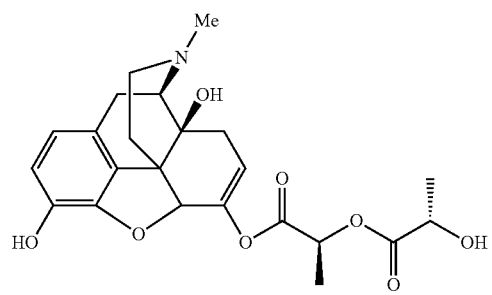
Formula 12
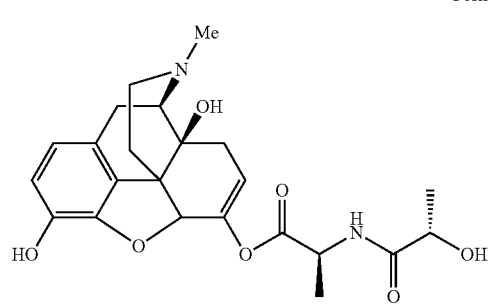
Formula 13
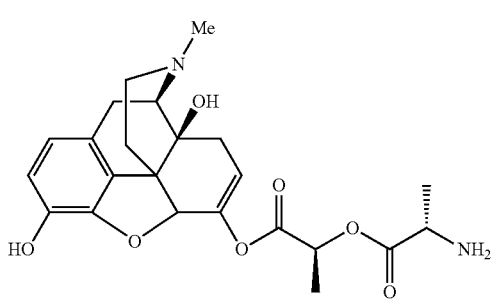
Formula 14
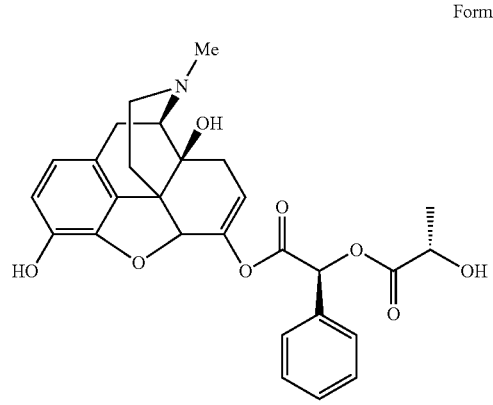
Formula 15
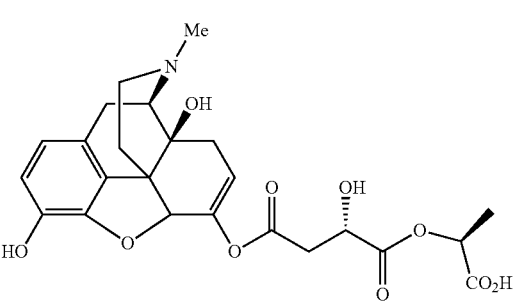

Formula 16
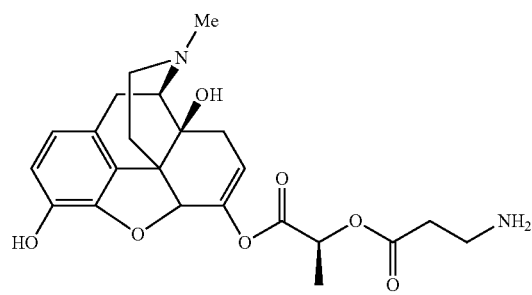
Formula 17
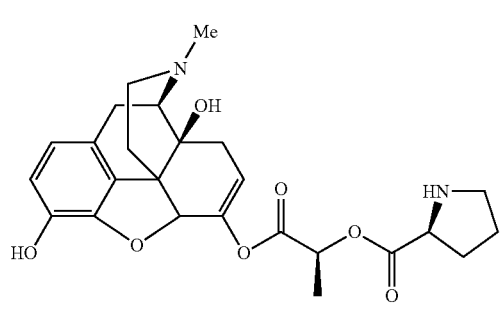
Formula 18
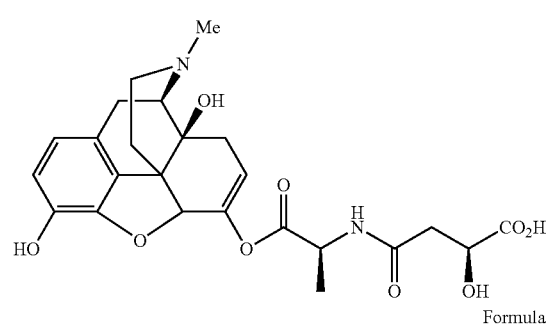
Formula 19
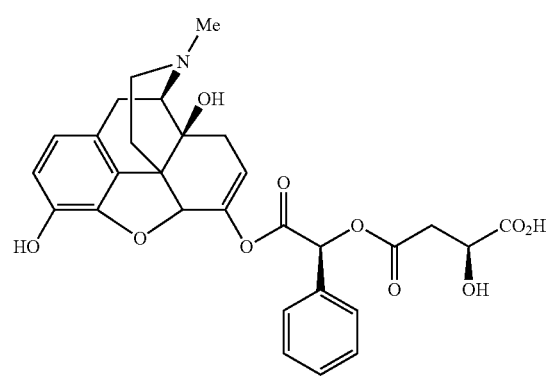
Formula 20
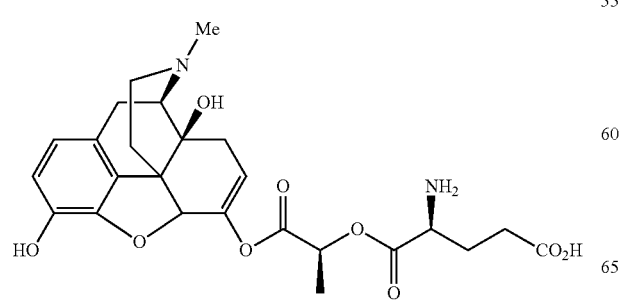
Formula 21
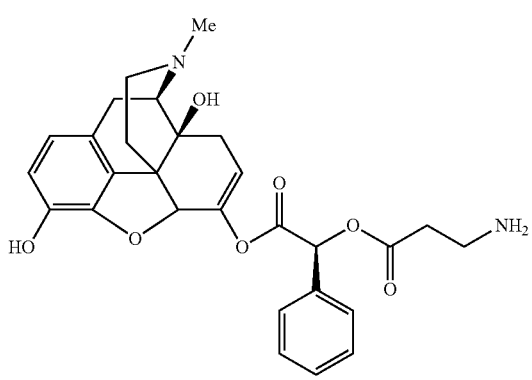
Formula 22
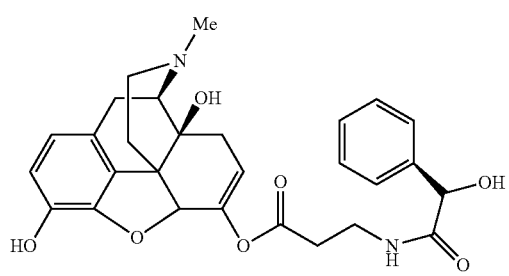
Formula 23
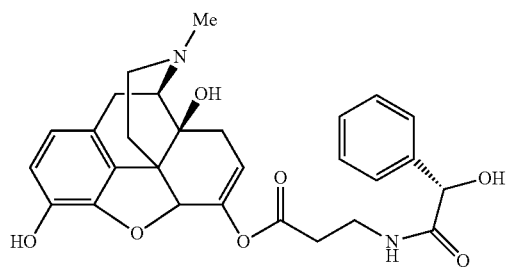
Formula 24
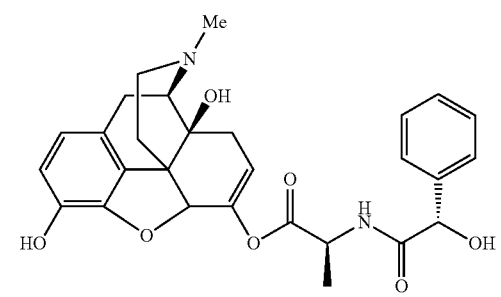
Formula 25
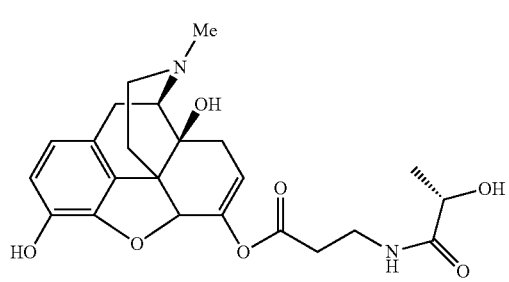

Formula 26
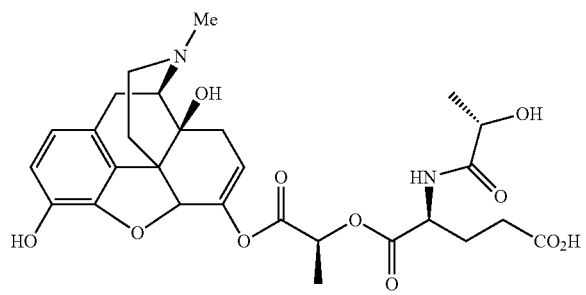
Formula 27
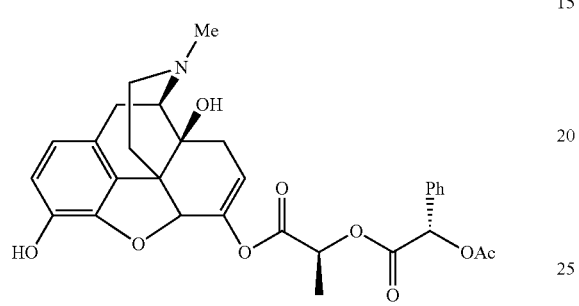
Formula 28
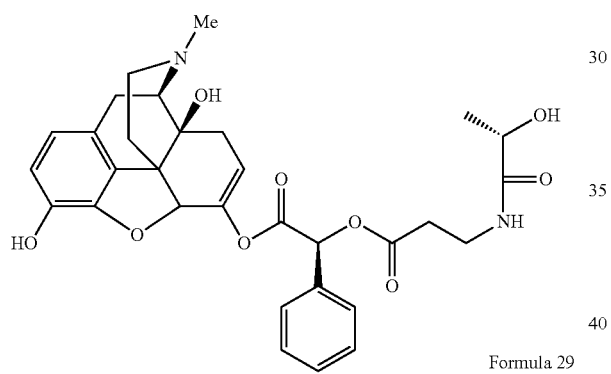
Formula 29
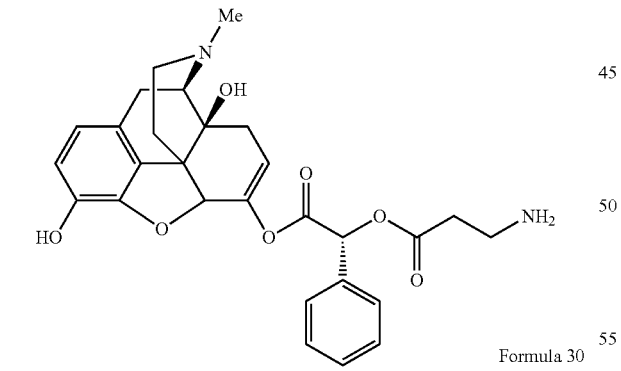
Formula 30
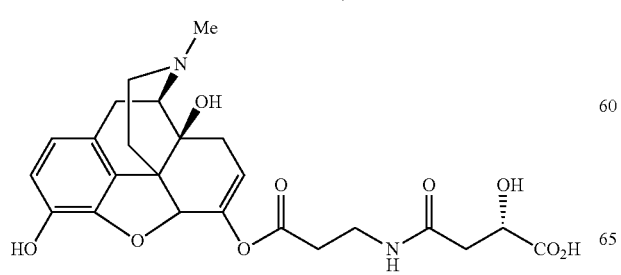
Formula 31
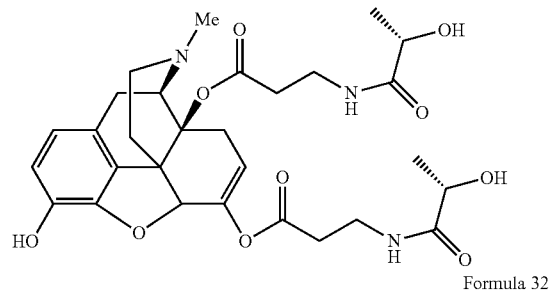
Formula 32
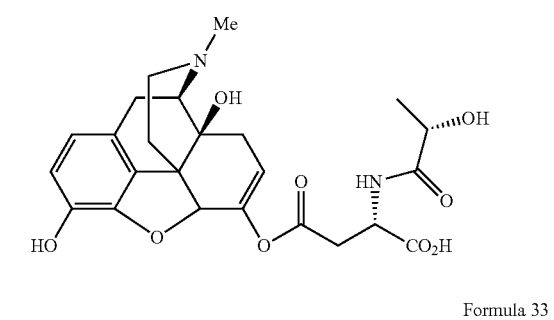
Formula 33
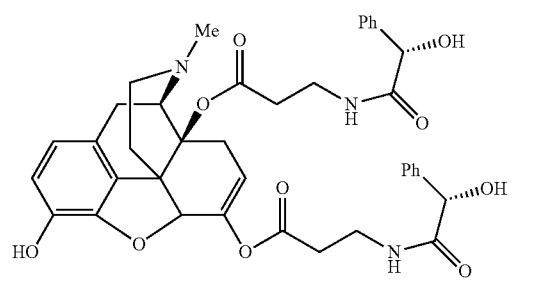
Formula 34
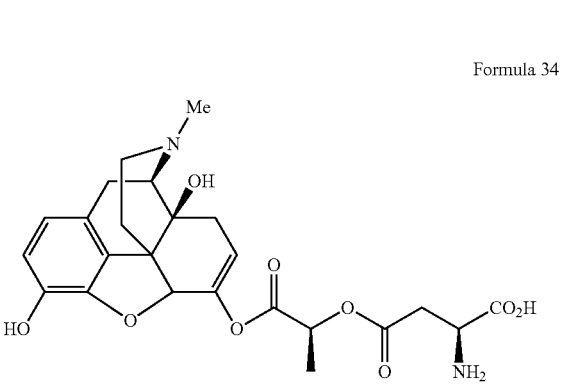
Formula 35
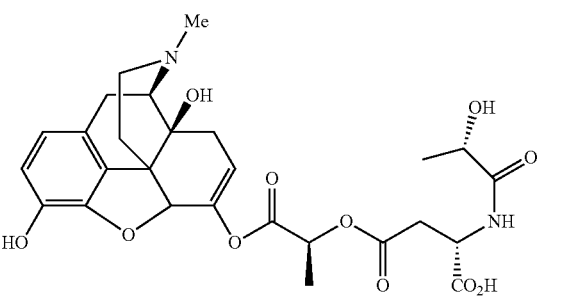

Formula 36
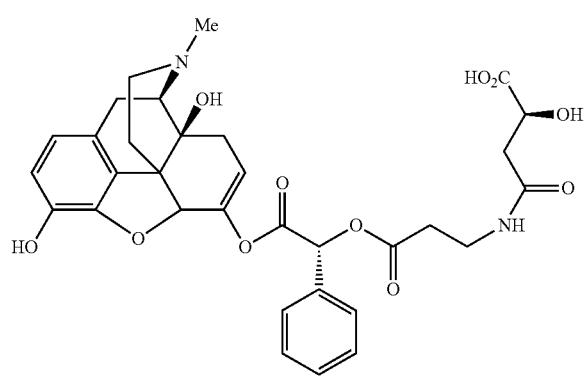
Formula 37
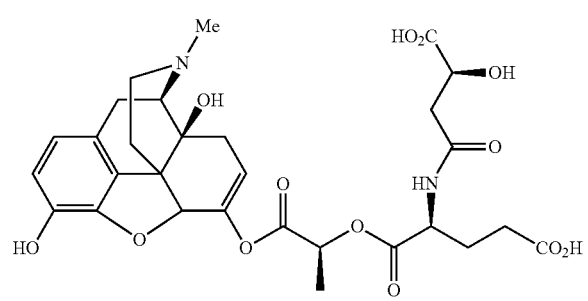
Formula 38
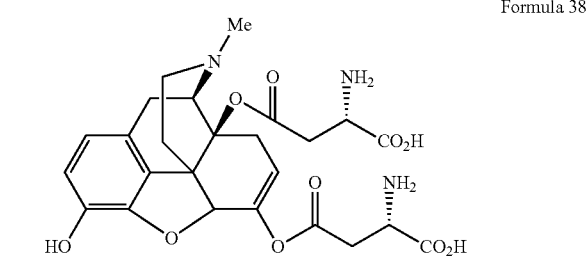
Formula 39
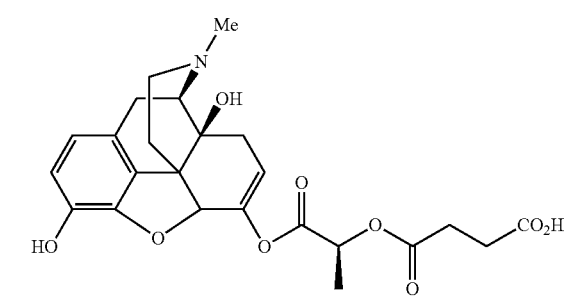
Formula 40
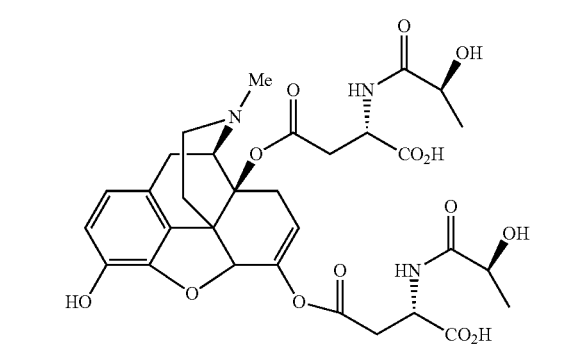
Formula 41
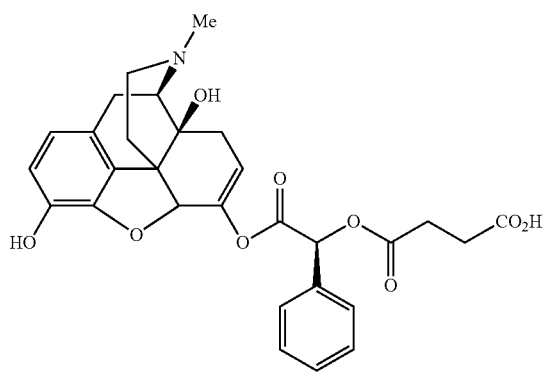
Formula 42
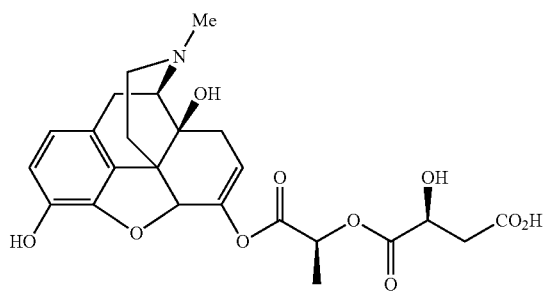
Formula 43
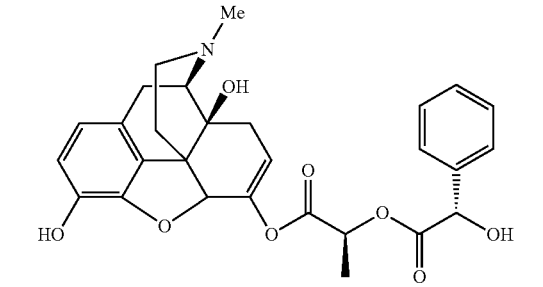
Formula 44
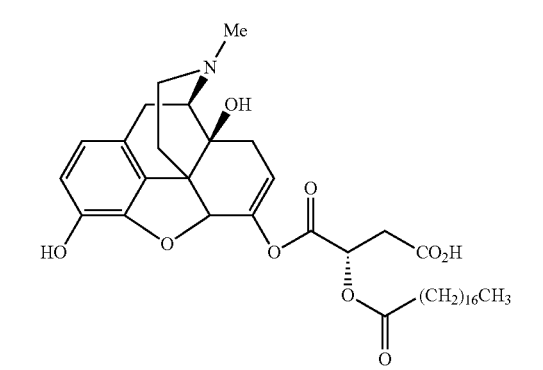
Formula 45
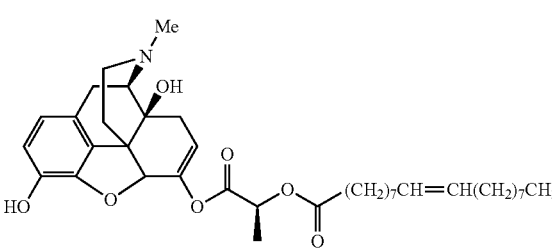

Formula 46
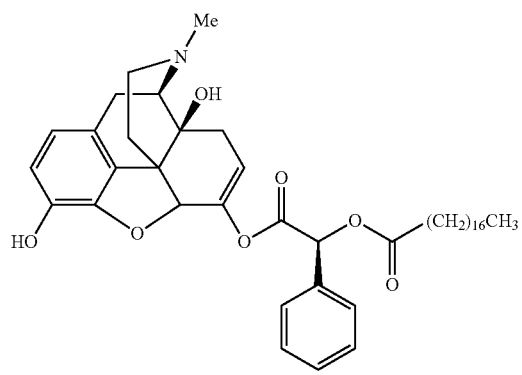
Formula 47
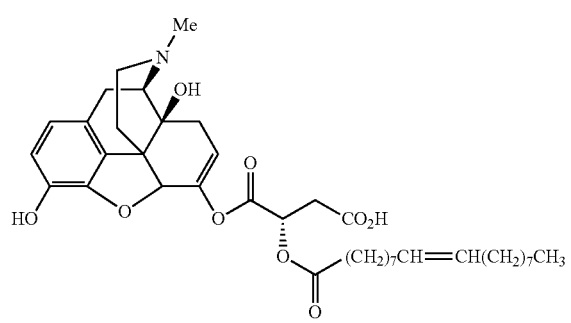
Formula 48
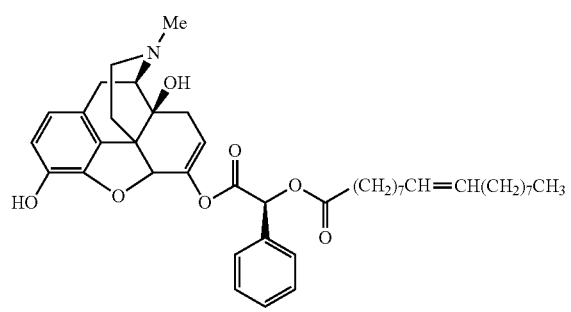
Formula 49
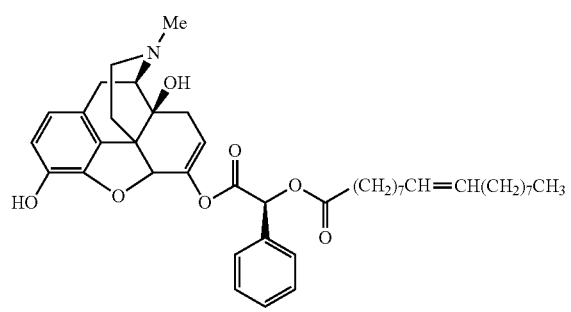
Formula 50
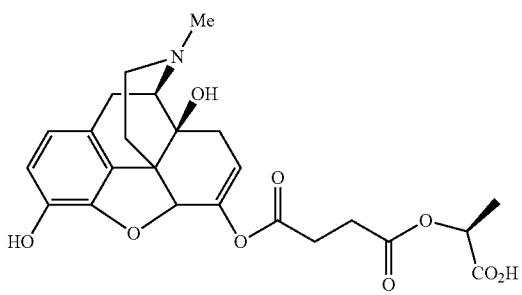
Formula 51
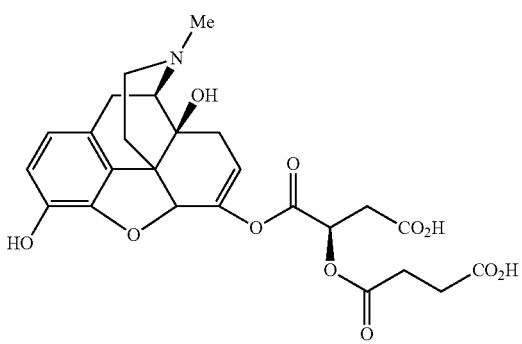
Formula 52
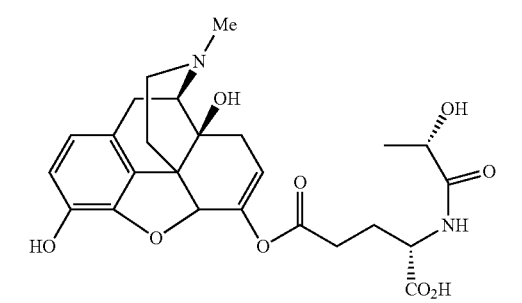
Formula 53
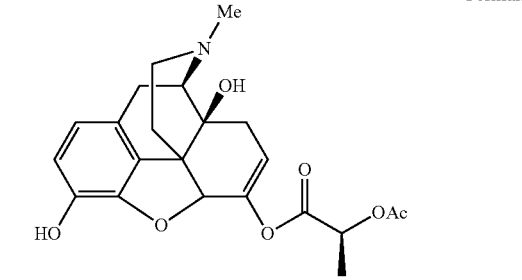
Formula 54
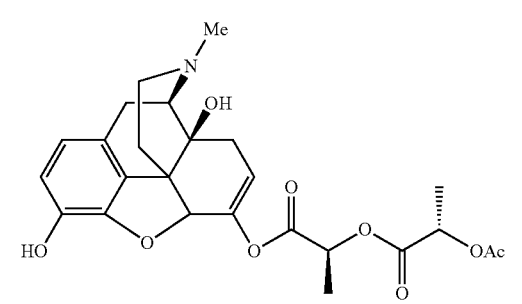

Formula 55
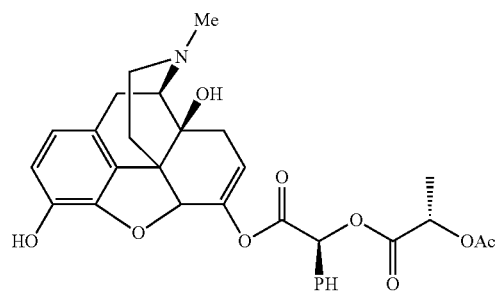
Formula 56
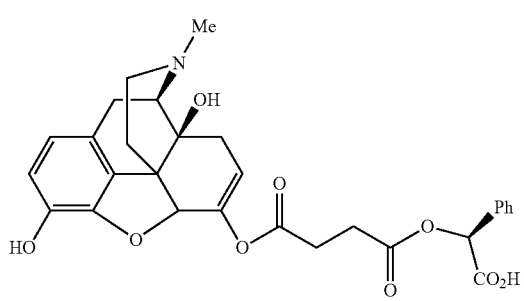
Formula 57
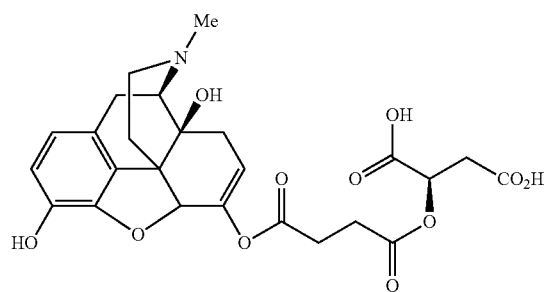
Formula 58
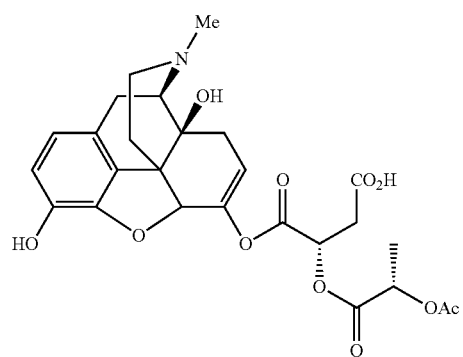
Formula 59
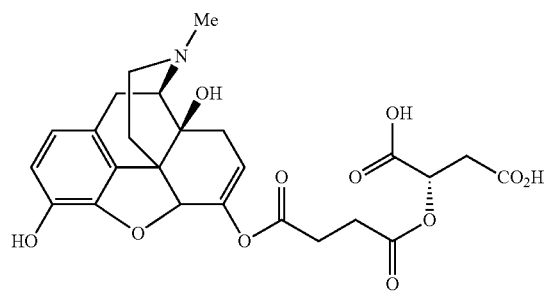
Formula 60
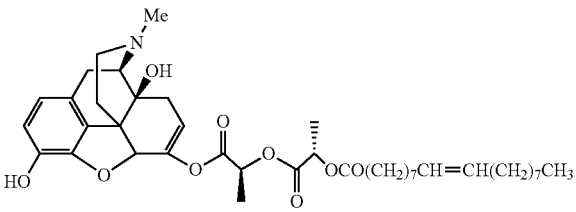
Formula 61
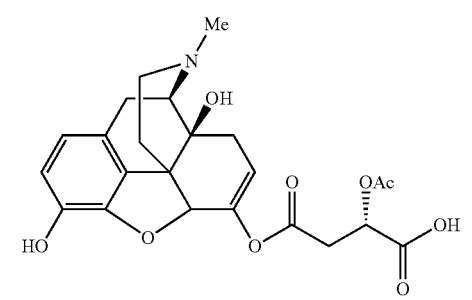
Formula 62
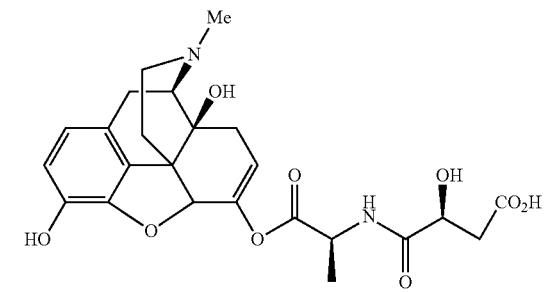
Formula 63
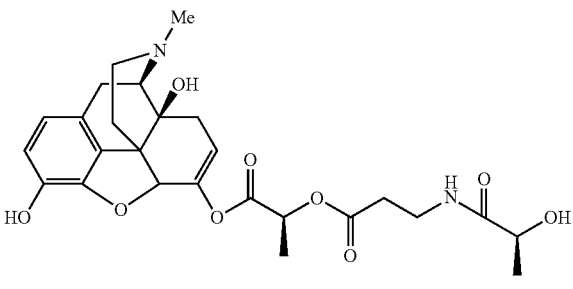
Formula 64
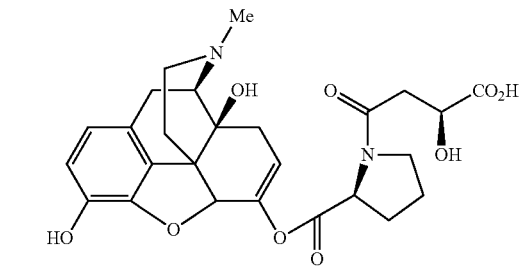

Formula 65
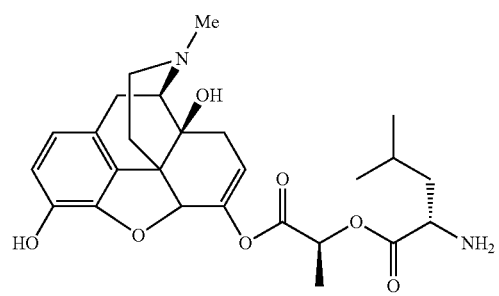
Formula 66
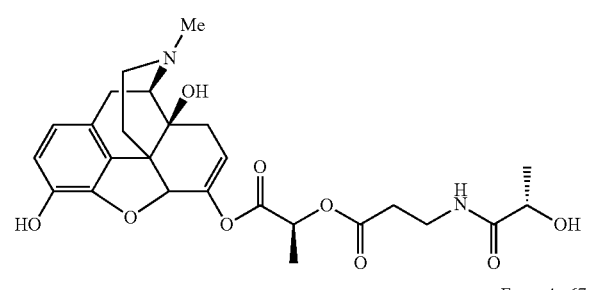
Formula 67
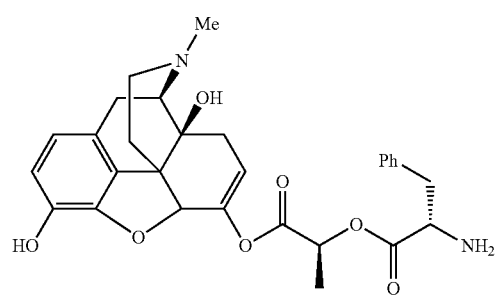
Formula 68
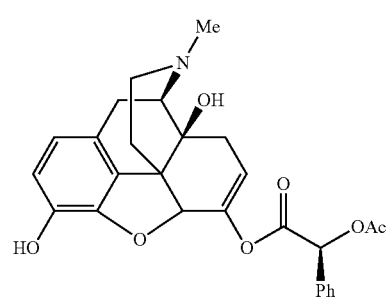
Formula 69
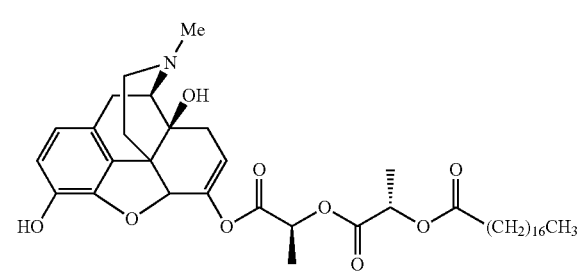
Formula 70
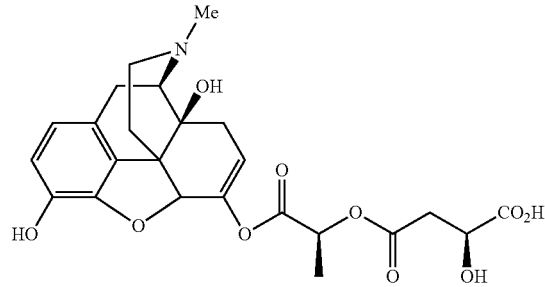
Formula 71
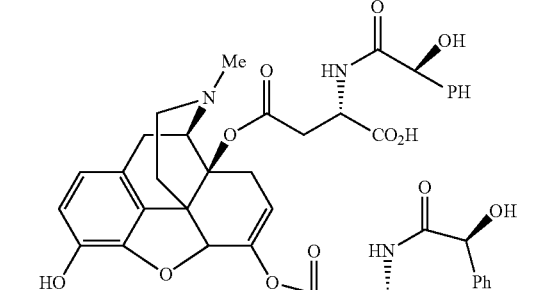
Formula 72
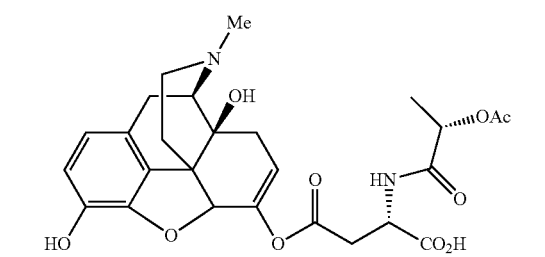
Formula 73
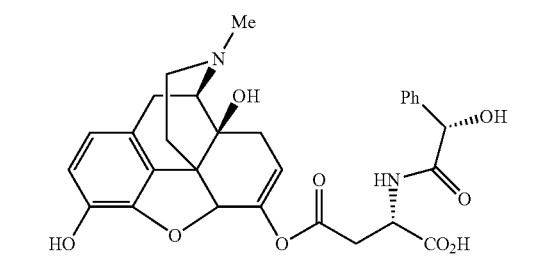
Formula 74
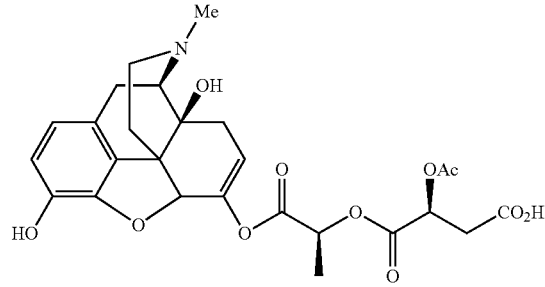

-continued
Formula 75
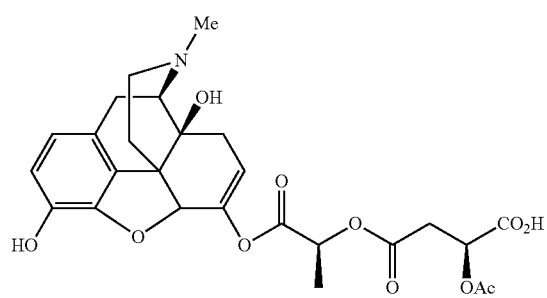
Formula 76
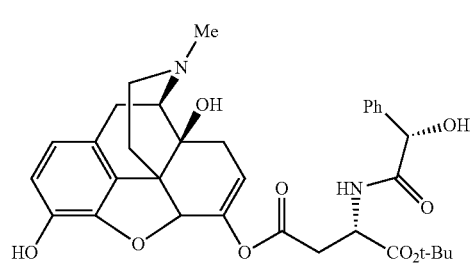
Formula 77
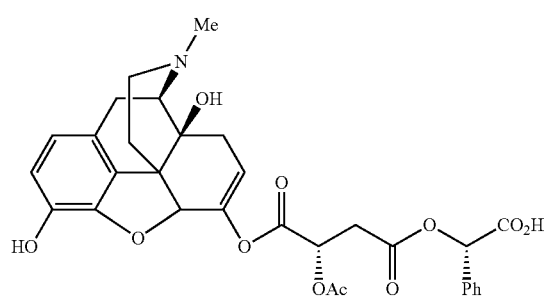
Formula 78
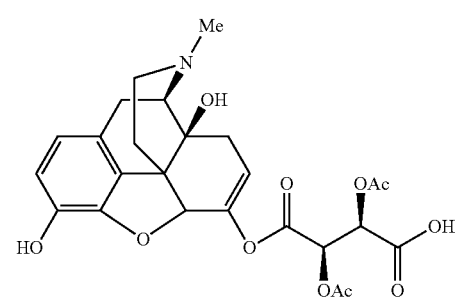
Formula 79
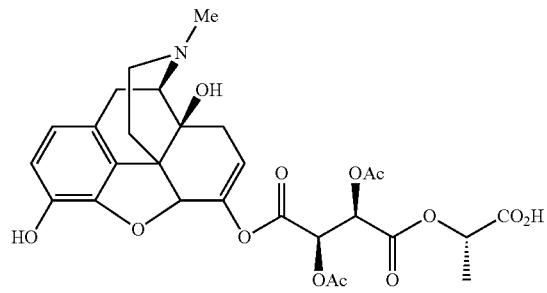
-continued
Formula 80
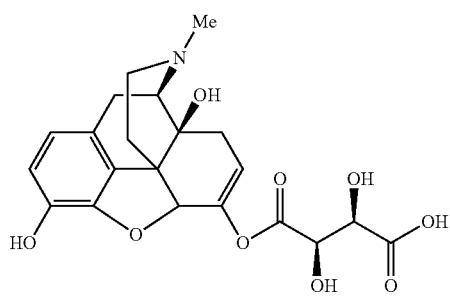
Formula 81
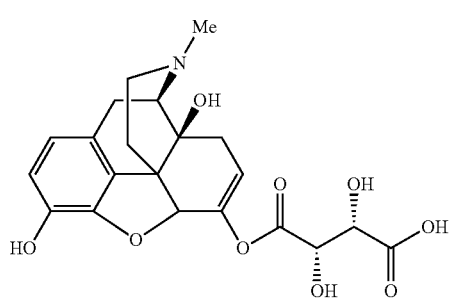
Formula 82
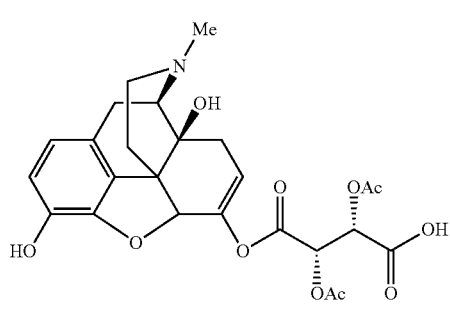
Formula 83
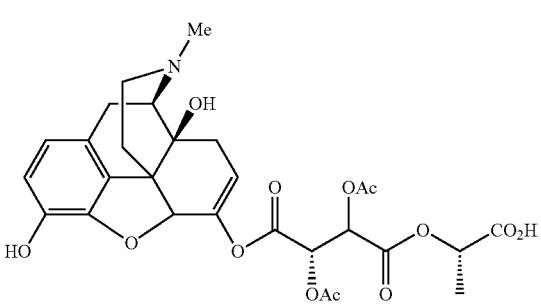
Formula 84
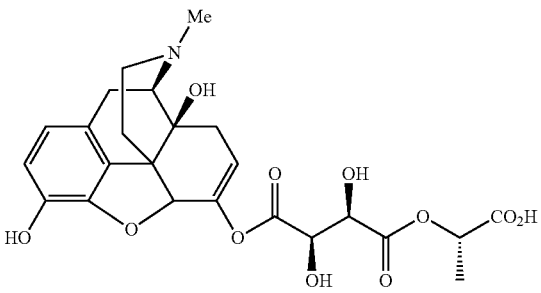

Formula 85

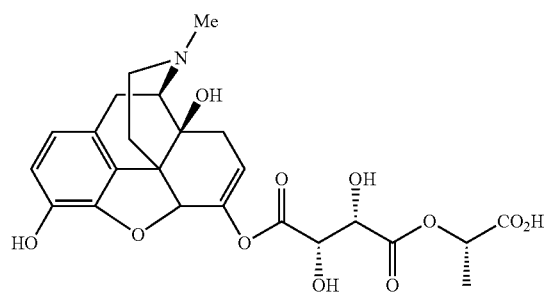

Formula 86

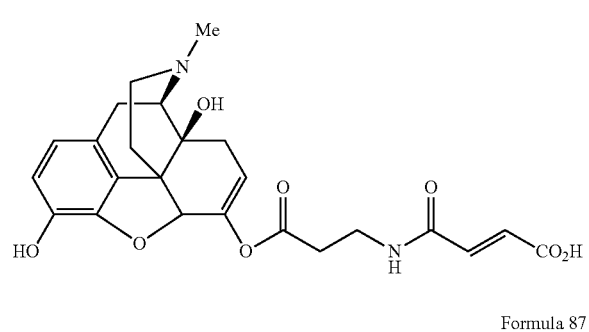

Formula 87

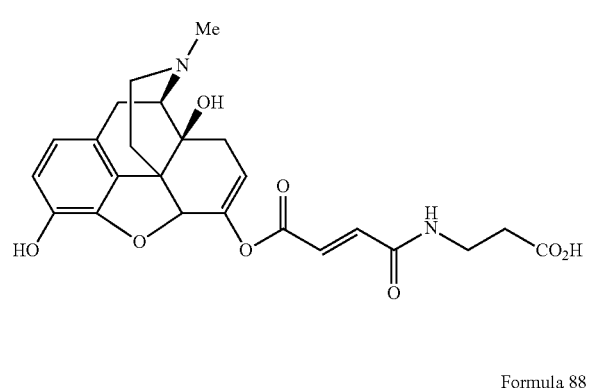

Formula 88

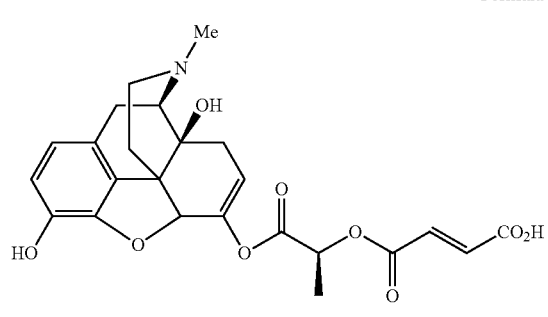

Formula 89

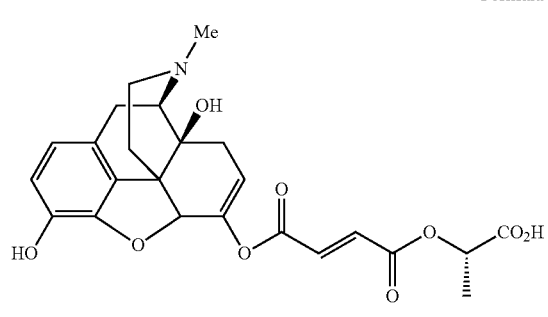

Formula 90

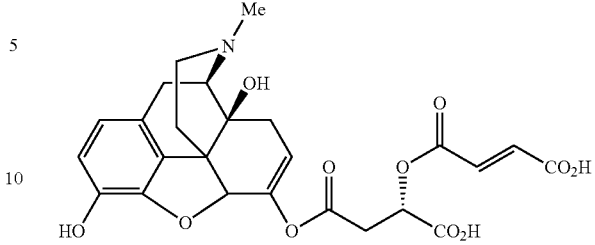

Formula 91

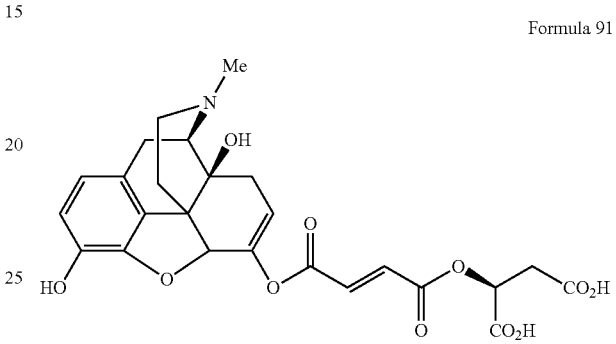

Formula 92

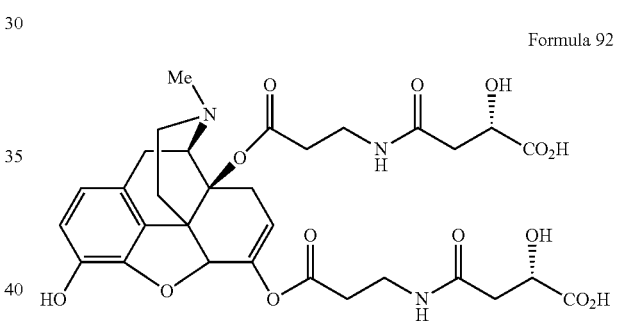

Formula 93

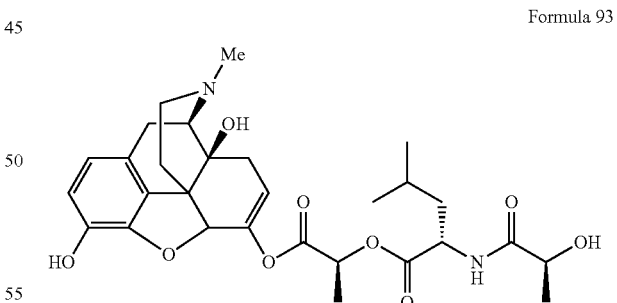

Embodiments

Various embodiments are listed below. It will be understood that the embodiments listed below may be combined with all aspects and other embodiments in accordance with the scope of the invention.

Embodiment 1: An oxymorphone prodrug of the following formula where the prodrug moiety X is attached covalently to the oxymorphone molecule via the 6 position ketone enolate oxygen as the enolate ester,

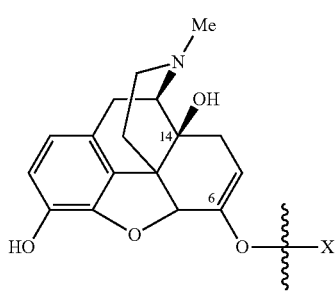

or a pharmaceutically acceptable salt thereof.

Embodiment 2: An oxymorphone prodrug of the following formula where the prodrug moiety X is attached covalently to the oxymorphone molecule via the 6 position ketone enolate oxygen as the enolate ester, and the prodrug moiety Y is attached covalently to the oxymorphone molecule via the 14 position hydroxyl oxygen as the alcohol ester,

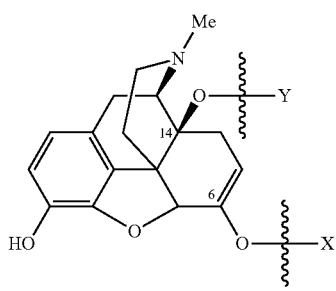

or a pharmaceutically acceptable salt thereof.

Embodiment 3: The oxymorphone prodrug of embodiment 2, wherein X and Y are the same or different.

Embodiment 4: The oxymorphone prodrug of embodiment 1 or 2, wherein X and Y are prodrug moiety ligands selected from alpha-hydroxy carboxylic acid and derivatives as monomers, alpha-hydroxy carboxylic acid homo-oligomers, alpha-hydroxy carboxylic acid hetero oligomers with another alpha-hydroxy carboxylic acid, alpha-hydroxy carboxylic acid hetero oligomers with amino acids, alpha-hydroxy carboxylic acid hetero oligomers with dicarboxylic acids, alpha-hydroxy carboxylic acid hetero oligomers with fatty acids, fatty acids, and other GRAS-based reagents.

Embodiment 5: The oxymorphone prodrug of embodiment 4 wherein homo- and hetero-'mers' are both linear and branched 'mers'. The homo- and hetero-'mers' are also cross linked with other GRAS reagents such as alpha-hydroxy carboxylic acid and amino acids.

Embodiment 6: The oxymorphone prodrug of embodiment 4 wherein the alpha-hydroxy carboxylic acid is lactic acid, tartaric acid, malic acid, citric acid, mandelic acid, pantoic acid, pantothenic acid and other poly-hydroxy carboxylic acids derived from sugars and carbohydrates. The naturally occurring (L)-isomers, the non-natural (D)-isomers, varying mixtures of (L) and (D) isomers, racemates and mixtures of diastereomers, and meso-isomers are all claimed in this invention.

Embodiment 7: The oxymorphone prodrug of embodiment 4 wherein the amino acids represented here are both natural (all 22 of the proteinogenic amino acids), and non-natural amino acids, the naturally occurring (L)-isomers, the non-natural (D)-isomers, varying mixtures of (L) and (D) isomers, racemates and mixtures of diastereomers. The amino acids represented here also include alpha amino acids, beta amino acids, gamma amino acids, and epsilon amino acids (amino group remote relative to the carboxyl group).

Embodiment 8: The oxymorphone prodrug of embodiment 4 wherein the fatty acids represented here are long chain carboxylic acids, ranging in lengths between eight carbons (C8) to twenty carbons (C20), and said fatty acids are linear or branched chains, and both saturated and non-non-saturated chains, and in the case of unsaturated fatty acids could be both cis- and trans-isomers (Z and E isomers), wherein examples of such fatty acids include, but are not limited to, sorbic acid, stearic acid, oleic acid, palmitic acid, and linoleic acid.

Embodiment 9: The oxymorphone prodrug of embodiment 4 wherein the dicarboxylic acids represented here to make hetero oligomers with alpha-hydroxy carboxylic acid include, but not limited to, fumaric acid, maleic acid, and succinic acid.

Embodiment 10: The oxymorphone prodrug of embodiment 1 or 2, wherein X and Y, if Y is present, are the same or different and is further represented as X is equal to ligands 1-16 and Y is equal to ligands 1-16 (shown below);

Ligand 1
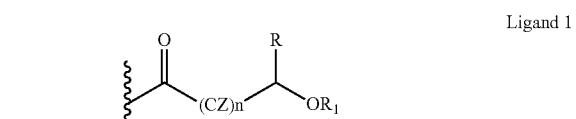

Ligand 2
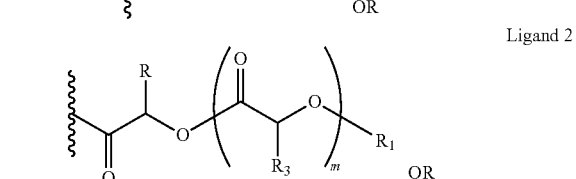

Ligand 3
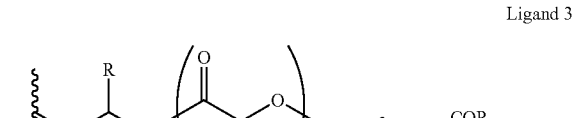

Ligand 4
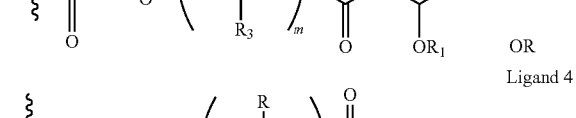

Ligand 5
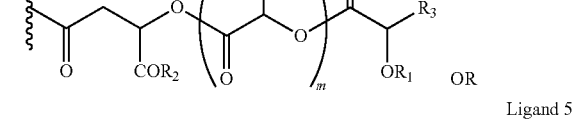

Ligand 6
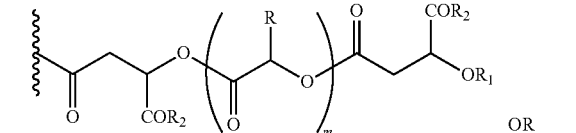

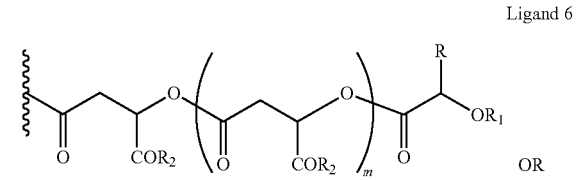

Ligand 7
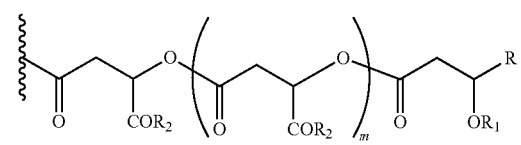

Ligand 8
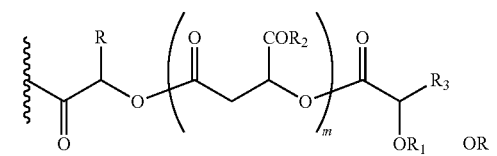

Ligand 9
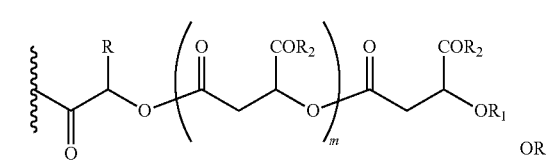

Ligand 10
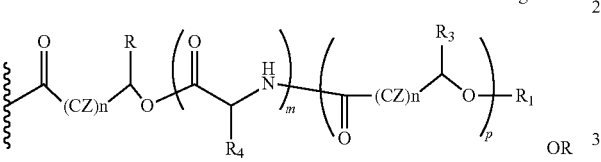

Ligand 11
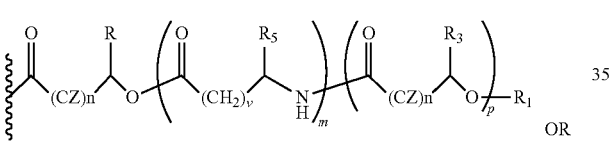

Ligand 12
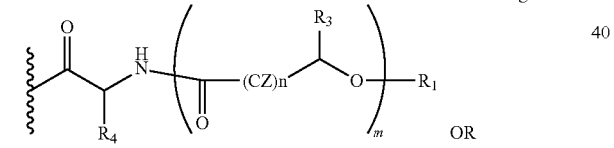

Ligand 13
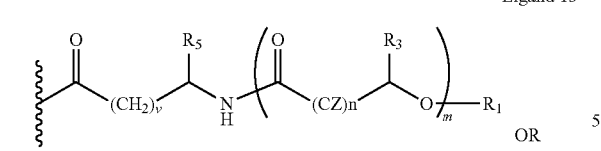

Ligand 14
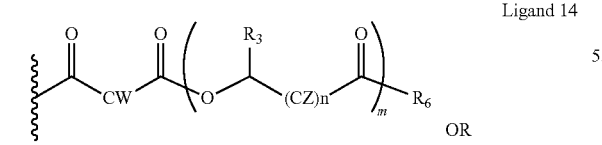

Ligand 15
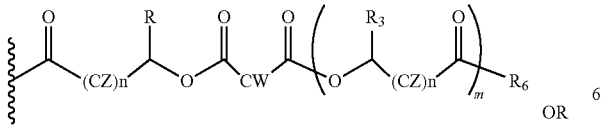

Ligand 16
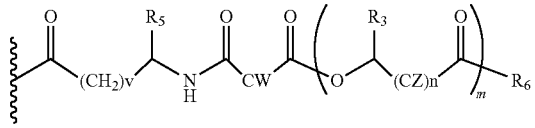

Wherein,
in ligands 1-16,
CZ=CH2, CHOR1,
R1=H, acyl groups from fatty acids, acyl groups from alpha-hydroxy acids, acyl groups from amino acids, and acyl groups from dicarboxylic acids including, but not limited to, fumaric acid, maleic acid and succinic acid,
R=Me, Ph, CH2COR2, CHOR1COR2, and COR2 (when n is not zero),
R2=OH, or is part of an ester formed by the hydroxyl group of another alpha-hydroxy acid or part of an amide formed by the amine group of an amino acid, and the amino acids represented here depicts both natural and non-non-natural amino acids, the naturally occurring (L)-isomers, the non-natural (D)-isomers, mixtures of (L) and (D) isomers, racemates and mixtures of diastereomers, or O-alkyl (alkyl esters, where the alkyl group is 1-4 carbon linear and branched, saturated and non-saturated alkyl groups),
R3=Me, Ph, CH2COR2, CHOR1COR2, and COR2 (when n is not zero),
R4 together with the adjacent nitrogen atom is part of an amino acid and the amino acids represented here depicts both natural and non-natural amino acids, the naturally occurring (L)-isomers, the non-natural (D)-isomers, mixtures of (L) and (D) isomers, racemates and mixtures of diastereomers (R4 in ligands 10 and 12),
R5=H, COR2,
CW=(CH2)q, CH=CH (both E and Z isomers),
R6=OH or is part of an ester formed by the hydroxyl group of another alpha-hydroxy acid or part of an amide formed by the amine group of an amino acid, or alkyl esters, and the amino acids represented here depicts both natural and non-natural amino acids, the naturally occurring (L)-isomers, the non-natural (D)-isomers, mixtures of (L) and (D) isomers, racemates and mixtures of diastereomers, or R6 is part of an ester with an alkyl group (O-alkyl, alkyl group is 1-4 carbon linear and branched, saturated and non-saturated alkyl groups),
and m is an integer selected from 0 to 4, and n is an integer selected from 0 to 2, and q is an integer selected from 2 to 6, and v is an integer selected from 0 to 6

Embodiment 11: The oxymorphone prodrug of embodiment 1 or 2, wherein X and Y, if Y is present, are the same or different and is further represented by ligand 17;

ligand 17
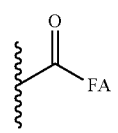

Wherein,
FA is C8 to C20 saturated fatty acids, C8 to C20 unsaturated fatty acids, including but not limited to, sorbic acid, stearic acid, oleic acid, palmitic acid, linoleic acid. These fatty acids could be both linear and branched chain fatty acids, and in the case of unsaturated fatty acids they could be both cis- and trans-isomers (Z and E isomers).

Embodiment 12: An oxymorphone prodrug compound represented by one of formulae 1-93.

Embodiment 13: A composition comprising the compound of any of embodiments 1-11.

Embodiment 14: The composition of embodiment 12, wherein the compound or pharmaceutically acceptable salts thereof maintains a steady-state release curve in blood that provides therapeutically effective oxymorphone bioavailability.

Embodiment 15: The composition of embodiment 12, wherein when said composition is administered orally and the bioavailability of oxymorphone is maintained.

Embodiment 16: A method of treating pain comprising orally administering the composition of embodiment 12 to a patient.

Embodiment 17: The pharmaceutical composition of embodiment 12, wherein the said composition is a pharmaceutically acceptable salt form.

Embodiment 18: A pharmaceutical composition comprising one or more of the oxymorphone prodrugs of embodiment 12 and one or more pharmaceutically acceptable excipients.

EXAMPLES

Processes for Preparing Mono-Substituted Oxymorphone Conjugates

Two general procedures have been used for the preparation of various mono substituted oxymorphone prodrug conjugates.

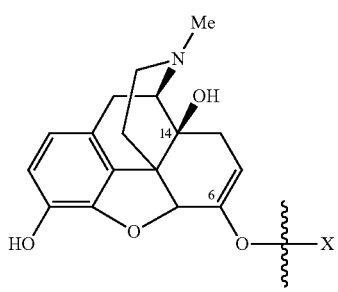

Formula A

The procedure involves treating tertiary-butoxy-carbonyl-oxymorphone (Boc-oxymorphone, wherein the phenolic OH group of oxymorphone is protected as a Boc [tertiary butoxy-carbonyl] group for the conjugation reactions) first with a base, followed by reacting the carboxyl-activated prodrug moieties and removing the Boc protecting group.

General Procedure 1:

Boc-oxymorphone coupling with the activated prodrug side chain; (lithium tertiary-butoxide [LiO$^t$Bu] procedure):

To a solution of opioid Boc-oxymorphone (1.4 g, 3.2 mmol) in tetrahydrofuran (THF) (10 mL) was added LiO$^t$Bu (1M solution in THF, 1.05 eq.) at 0° C., then stirred at ambient temperature for 30 min. The brown solution was cooled down to −78° C. and a solution of tertiary butoxy-carbonyl-hydroxyl protected carboxyl N-hydroxy succinimide-active ester (Boc-hydroxyl protected Osu-active ester) of alpha-hydroxy acid (1.05 g, 3.4 mmol) in THF (20 mL) was added over a period of 5 mins. After stirring the reaction at −78° C. for 30 minutes, it was allowed to warm to room temperature (RT) over a period of 3 hrs. The turbid reaction mixture was poured into saturated (satd) ammonium chloride (NH$_4$Cl) solution (150 mL), stirred for 5 mins and extracted with ethyl acetate (EtOAc) (250 mL). The organic part was washed with aqueous (aq) NH$_4$Cl, aq. Sodium bicarbonate (NaHCO$_3$), brine, dried over anhydrous sodium sulphate (Na$_2$SO$_4$) and evaporated to dryness to give Boc-protected oxymorphone product (1.9 g, purity ~90%).

In some cases the crude product is used as such for the next tertiary butoxy-carbonyl (Boc) de-protection step or it may be further purified by standard column chromatography before the deprotection of the Boc group from the phenolic group of Boc-oxymorphone and the Boc- group from the hydroxyl group of the ligand.

The product was further characterized by nuclear magnetic resonance (NMR) spectroscopy, mass spectroscopy (MS) and elemental analysis.

General Procedure 2:

Boc-oxymorphone coupling with the activated prodrug side chain; (LHMDS [lithium hexamethyl disilaside] procedure):

To a solution of opioid oxymorphone (1.4 g, 3.2 mmol) in THF (10 mL) was added LHMDS (i.e., LiN(TMS)$_2$, i.e., lithium hexamethyl disilaside) (1M solution in THF, 1.05 eq.) at 0° C., then stirred at ambient temperature for 30 min. The brown solution was cooled down to −78° C. and a solution of Boc-hydroxyl protected Osu-active ester of alpha-hydroxy acid (1.05 g, 3.4 mmol) in THF (20 mL) was added over a period of 5 mins. After stirring the reaction at −78° C. for 30 minutes, it was allowed to warm to room temperature (RT) over a period of 3 hrs. The turbid reaction mixture was poured into satd NH$_4$Cl solution (150 mL), stirred for 5 mins and extracted with EtOAc (250 mL). The organic part was washed with aqueous (aq) NH$_4$Cl, aq. NaHCO$_3$, brine, dried over Na$_2$SO$_4$ and evaporated to dryness to yield the product (1.85 g, purity ~95%).

The crude product may contain trace amounts of the bis-series of the prodrug.

In some cases the crude product is used as such for the next de-protection step or it may be further purified by standard column chromatography before the deprotection of the Boc group from the phenolic group of Boc-oxymorphone and the Boc- group from the hydroxyl group of the ligand.

The product was further characterized by NMR, MS and elemental analysis.

Process for Preparing Di-Substituted Oxymorphone Conjugates

A general procedure has been used for the preparation of various di-substituted oxymorphone prodrug conjugates (X═Y).

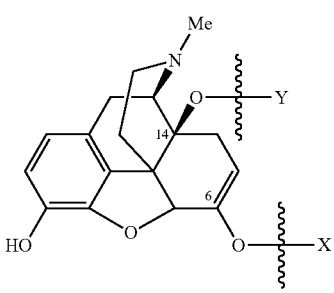

Formula B

The procedure involved treating Boc-oxymorphone first with excess base followed by reacting with excess carboxyl-activated prodrug moieties.

General Procedure:

Boc-oxymorphone coupling with the activated prodrug side chain, (LHMDS procedure to prepare the di-substituted Boc-oxymorphone prodrug conjugates):

To a solution of opioid Boc-oxymorphone (1.4 g, 3.2 mmol) in THF (15 mL) was added LHMDS (LiN(TMS)$_2$, Lithium hexamethyl disilaside) (1M solution in THF, 2.5 eq.) at 0° C., then stirred at ambient temperature for 30 min. The brown solution was cooled to −78° C. and a solution of Boc-hydroxyl protected Osu-active ester of alpha-hydroxy acid (2.2 g, 6.9 mmol) in THF (20 mL) was added over a period of 5 mins. After stirring the reaction at −78° C. for 30 minutes, it was allowed to warm to room temperature (RT) over a period of 3 hrs. The turbid reaction mixture was poured into satd NH$_4$Cl solution (150 mL), stirred for 5 mins and extracted with EtOAc (250 mL). The organic part was washed with aqueous (aq) NH$_4$Cl, aq. NaHCO$_3$, and brine, dried over Na$_2$SO$_4$ and evaporated to dryness to give the crude product (2.5 g). The crude product as the Boc-oxymorphone conjugate may contain small amounts of the corresponding mono-series prodrug, along with bis-series of the prodrug, as the main components. The crude product was further purified and separated the mono- and bis-products by standard column chromatography.

The product was further characterized by NMR, MS and elemental analysis.

Tertiary butoxy-carbonyl (Boc) Group Deprotection from the Coupled enol-ester Prodrug Product:

This deprotection removes both the Boc-protecting groups from the phenolic OH group of oxymorphone and the Boc-protecting group from the hydroxyl group(s) of the alpha-hydroxy carboxylic acid ligands. Boc group protection was used to protect the hydroxyl group(s) of the alpha-hydroxy carboxylic acids before coupling. After the Boc-oxymorphone coupling, all the Boc groups were removed by the following general procedure.

To a solution of the fully Boc- protected coupled product (2.5 g) in iso-propyl acetate (IPAc) (15 mL) was added 4N HCl/dioxane (15 mL) and the reaction mixture was stirred at RT for 3 h (white precipitate [ppt] formation takes place after 10-15 mins). The solution was diluted with IPAc (50 mL) and stirred for 10 mins. The precipitate was filtered, washed with IPAc and dried to give the deprotected product (quantitative yield). In this case the product is isolated as the HCl salt. HPLC purity ~95%.

The product was further characterized by NMR, MS and elemental analysis.

Boc Groups Deprotection from the Coupled enol-ester Prodrug Product; (Another General Procedure):

A second general procedure was also used to remove all of the Boc groups from the coupled enol-ester prodrug product. To a solution of the fully Boc- protected coupled product (2.5 g) in dichloromethane (15 mL) was added trifluoro acetic acid (15 mL) and the reaction mixture was stirred at RT for 3 hrs. The reaction mixture was concentrated to a dry powder on a rotavap and the residue was further purified by either trituration or chromatography as a TFA salt of the enol ester prodrug product. In this case the product is isolated as the TFA salt. HPLC purity ~95%.

The product was further characterized by NMR, MS and elemental analysis.

Synthesis of the carboxyl-N-hydroxy succinimide (—OSu ester) Activated Side Chain for Boc-oxymorphone Coupling:

Generally, N-hydroxy succinimide ester activated carboxylic acid of the Boc protected alpha-hydroxy carboxylic acid was used for Boc-oxymorphone coupling. To a solution of the hydroxyl Boc-protected alpha-hydroxy carboxylic acid (1 g, 1.1 mmol) and N-hydroxy succinimide (NHS) (1.05 eqv) in THF (10 mL) was added a solution of di-cyclohexyl carbodiimide (DCC) (1.05 eqv) in THF (5 mL) at 0° C. The reaction mixture was slowly brought to RT and left overnight at RT. The turbid solution was filtered and the filtrate was used as such for the next step coupling process.

(Depending on specific compound stability, the OSu ester also can be precipitated and crystallized).

Bioavailability Studies of Oxymorphone Prodrug Conjugates

The invention is further demonstrated by pharmacokinetic (PK) studies with oxymorphone that has been modified by the covalent attachment of various GRAS-based prodrug moieties at 6 and 14 oxygen positions of oxymorphone. Studies include PK evaluations of the various drug conjugates administered by the oral route.

Oral bioavailability studies of oxymorphone compared with oxymorphone conjugates were conducted in male Sprague-Dawley rats. Doses of oxymorphone hydrochloride and oxymorphone conjugates containing equivalent amounts of oxymorphone were administered in deionized water.

Male Sprague-Dawley rats were provided water ad libitum, fasted overnight and dosed by oral gavage with oxymorphone conjugates or oxymorphone HCl. All doses contained equivalent amounts of oxymorphone base. Plasma oxymorphone concentrations were measured by LC/MS.

Rat oral PK profile of oxymorphone of these oxymorphone prodrug conjugates are shown in FIGS. 1-42. Oxymorphone HCl, 3.54 mg/kg was used as the reference and all the prodrug compounds weights were adjusted to 3.54 mg/kg oxymorphone HCl equivalent weight.

What is claimed:

1. An oxymorphone prodrug of the following formula where the prodrug moiety X is attached covalently to the oxymorphone molecule via the 6 position ketone enolate oxygen as the enolate ester,

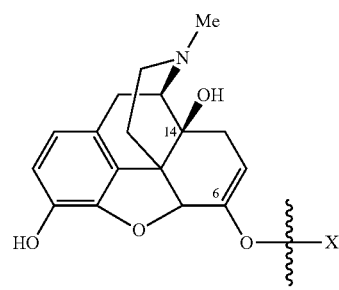

or a pharmaceutically acceptable salt thereof, wherein X is malic acid covalently attached to the oxymorphone.

2. An oxymorphone prodrug compound represented by any one of

Formula 1

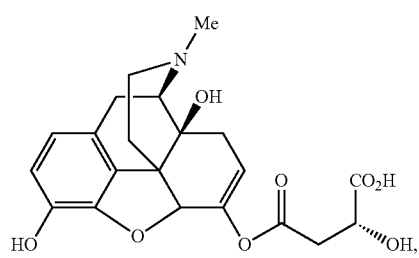

Formula 4

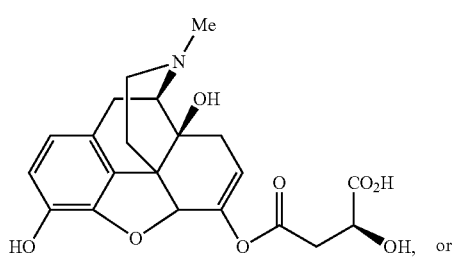 or

Formula 10

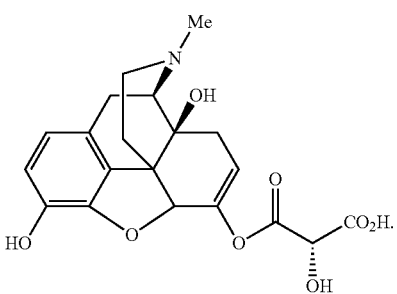

3. A pharmaceutical composition comprising one or more of the oxymorphone prodrugs according to claim 2 and one or more pharmaceutically acceptable excipients.

4. An oral pharmaceutical composition comprising the compound of claim 1 and a pharmaceutically acceptable excipient.

5. The pharmaceutical composition of claim 4, wherein the compound is a pharmaceutically acceptable salt form.

6. A method of treating pain comprising orally administering the composition of claim 4 to a patient.

* * * * *